(12) United States Patent
Cohen et al.

(10) Patent No.: US 7,517,856 B2
(45) Date of Patent: Apr. 14, 2009

(54) BIOCONJUGATES COMPRISING SULFATED POLYSACCHARIDES AND THEIR USES

(75) Inventors: Smadar Cohen, Beer Sheva (IL); Inbar Freeman, Doar Na Ha'negev (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 120 days.

(21) Appl. No.: 11/374,279

(22) Filed: Oct. 11, 2005

(65) Prior Publication Data

US 2007/0081976 A1 Apr. 12, 2007

(51) Int. Cl.
*A61K 38/00* (2006.01)
*C07K 14/00* (2006.01)

(52) U.S. Cl. .............................. 514/12; 514/2; 530/350
(58) Field of Classification Search ........................ None
See application file for complete search history.

(56) References Cited

U.S. PATENT DOCUMENTS 4,178,361 A * 12/1979 Cohen et al. ................. 424/487
6,388,060 B1   5/2002 Guo et al.

FOREIGN PATENT DOCUMENTS

| EP | 1886696 A1 | 2/2008 |
|---|---|---|
| WO | 8912464 A1 | 12/1989 |
| WO | 9921588 A1 | 5/1999 |
| WO | 0064481 A1 | 11/2000 |
| WO | 0166164 A1 | 9/2001 |

OTHER PUBLICATIONS

Paredes et al., "Mechanisms Responsible for Catalysis of the Inhibition of Factor Xa or Thrombin by Antithrombin Using a Covalent Antithrombin-Heparin Complex", The Journal of Biological Chemistry 278: 23398-23409 (2003).*
Web link to Wikipedia: en.wikipedia.org/wiki/Iduronic_acid dowloaded Sep. 4, 2007.*
Kreuger et al., "Characterization of fibroblast growth factor 1 binding heparan sulfate domain", Glycobiology 9(7): 723-729 (1999).*
Habuchi et al., "Structure of a heparan sulfate oligosaccharide that binds to basic fibroblast growth factor", 285: 805-813 (1992).*
Inbar Freeman et al., "Alginate-Sulfate As A Substitute For Heparan Sulfate-Studies On Binding And Controled Delivery Of Angiogenic Factors", *Abstract Book of the Joint Meeting of the Tissue Engineering Society International and European Tissue Engineering Society*, Lausanne, Switzerland, Oct. 10-13, 2004—a one- page abstract published by the inventors one year before filing date of the application.
Siska Cochran et al., "Probing the Interactions of Phosphosulfomannans with Angiogenic Growth Factors by Surface Plasmon Resonance", *J. Med. Chem.*, vol. 46, pp. 4601-4608, 2003.
Schroeder-Tefft et al., Collagen and heparin matrices for growth factor delivery, Journal of Controlled Release, 48:29-31 (1997).

* cited by examiner

*Primary Examiner*—Anand U Desai
(74) *Attorney, Agent, or Firm*—Bowdy and Neimark, PLLC

(57) ABSTRACT

The present invention provides bioconjugates comprising a sulfated polysaccharide such as alginate sulfate and hyaluronan sulfate and at least one bioactive polypeptide capable of binding a sulfate group of said sulfated polysaccharide. The bioactive polypeptide can be a heparin-binding polypeptide and/or a positively-charged polypeptide. Also, provided are delivery systems and methods for sustained release of said bioactive polypeptide(s) using said bioconjugates.

23 Claims, 29 Drawing Sheets

BIOCONJUGATES COMPRISING SULFATED POLYSACCHARIDES AND THEIR USES

FIELD OF THE INVENTION

The present invention relates to sulfated polysaccharides and to bioconjugates comprising them as delivery systems for sustained release.

Abbreviations: AP: amyloid P; ApoE: apolipoprotein E; AT III: antithrombin III; C1 INH: C1 esterase inhibitor; CS: circumsporozoite; CXCL4: CXC chemokine ligand 4; CypA: cyclophilin A; EGF: epidermal growth factor; FGF: fibroblast growth factors; HB-GAM: heparin-binding growth-associated molecule; HGF: hepatocyte growth factor; HIV-1: immunodeficiency virus type-1; HSV: herpes simplex virus; IGF: insulin-like growth factor; IL-6: interleukin-6; IL-8: interleukin-8; MCP-1: monocyte chemoattractant protein-1; MIP-1: macrophage inflammatory peptide-1; RANTES: regulated on activation, normal T expressed and secreted; SDF-1: stromal cell-derived factor-1; SLP1: serine protease inhibitor; TPO: thrombopoietin; TSR: thrombospondin type I repeat; VCP: Vaccinia virus complement control protein; VEGF: vascular endothelial growth factor.

BACKGROUND OF THE INVENTION

Controlled-release dosage forms are designed to reduce drug-dosing frequency and to reduce fluctuation in plasma drug concentration, providing a more uniform therapeutic effect. Less frequent dosing is more convenient and may improve patient compliance. These dosage forms are suitable for drugs that otherwise require frequent dosing because elimination half-life and duration of effect are short.

Man-made controlled release dosage forms, such as hydrogels and solid polymeric microspheres, usually rely on drug release mechanisms that are based on passive diffusion, polymer degradation or passive diffusion coupled with polymer degradation. Examples of these systems include polyester microspheres or alginate hydrogels.

On the other hand, nature's way of devising controlled release dosage forms is based on principles of biological specificity. A known example to this is the biomolecular interactions between heparin/heparan sulfate and heparin-binding peptides, e.g. growth factors. These interactions form a depot for growth factor storage in the tissues. Upon tissue injury, the growth factors are released and induce processes associated with wound healing.

For years, we and others have been investigating the use of alginate hydrogels for the controlled delivery of drugs and as scaffolds for tissue engineering.

Alginate is a polysaccharide derived from brown seaweed. It is an anionic polysaccharide composed of uronic acids (guluronic (G) and mannuronic (M) acids) that undergoes gelation in the presence of bivalent cations, such as $Ca^{2+}$ and $Ba^{2+}$. In the pharmaceutical/medicinal fields, it is used successfully as encapsulation material, mostly for cells (bacterial, plant and mammalian cells). For molecules, it is much less effective, and even macromolecules in size of 250 kDa are rapidly released from alginate hydrogel systems. In particular, biological molecules of interest such as cytokines, growth factors, with sizes ranging between 5 to 100 kDa, are rapidly released.

Thus, there is a need for modification/s in polysaccharides such as alginate for their use in the controlled delivery of drugs.

SUMMARY OF THE INVENTION

It has now been found according to the present invention that a bioconjugate comprising a sulfated polysaccharide, such as alginate sulfate and hyaluronan sulfate, and at least one bioactive peptide capable of binding a sulfate group of said sulfated polysaccharide, can direct the sustained release of said at least one bioactive peptide from said bioconjugate.

Thus, the present invention relates to a bioconjugate comprising a sulfated polysaccharide and at least one bioactive polypeptide capable of binding a sulfate group of said sulfated polysaccharide.

The present invention further relates to a pharmaceutical composition comprising a bioconjugate of the invention, in particular, as a delivery system for sustained release of bioactive polypeptide(s).

The present invention relates also to pharmaceutical compositions comprising sulfated polysaccharides and a pharmaceutically acceptable carrier, for treatment or inhibition of a disease or disorder caused by, or associated with, the activity of at least one bioactive polypeptide capable of binding a sulfate group of said sulfated polysaccharide.

Also provided is a method for treatment of a patient suffering from a disease or disorder caused by, or associated with, the activity of at least one bioactive polypeptide capable of binding a sulfate group of a sulfated polysaccharide, which comprises administering to said patient an effective amount of sulfated alginate, sulfated hyaluronan, or both.

BRIEF DESCRIPTION OF THE FIGURES

FIGS. 25A1-A3, B1-B3, C1-C3 show immunohistochemistry staining for αSMA (smooth muscle actin) (25A1, 25B1, and 25C1), α-Lectin (endothelial cells) (25A2, 25B2, 25C2), and ED1 (macrophages) (25A3, 25B3, 25C3) of the capsule surrounding the implanted scaffolds. (25A) alginate/alginate sulfate/bFGF. (25B) alginate/bFGF and (25C) alginate/alginate sulfate. (bar indicates 100 µm).

DETAILED DESCRIPTION OF THE INVENTION

Figure 1:
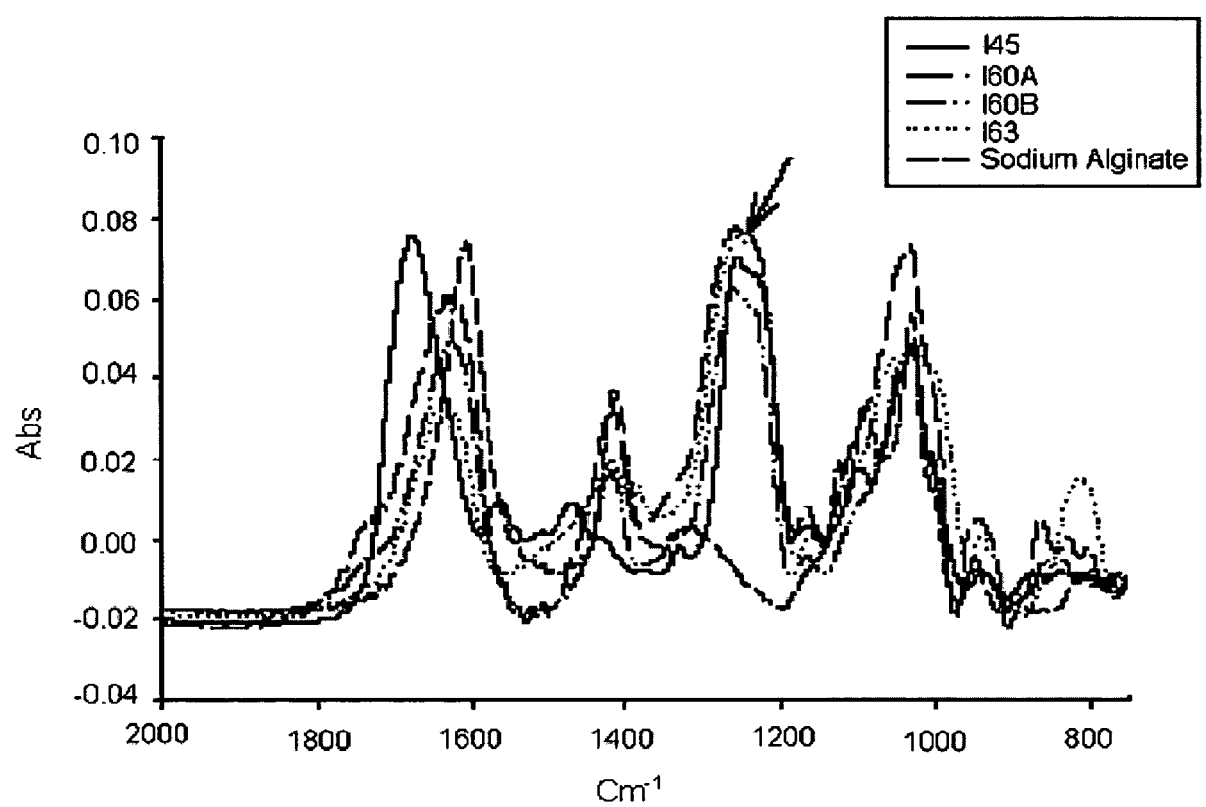
FIG. 1 shows FTIR spectra of alginate sulfate (I-49, I-60A, I-60B and I-63) and raw material sodium alginate. The arrow point towards a new major peak at $\sim 1250\ cm^{-1}$ proving controlled sulfation of alginate.
Figure 2A:
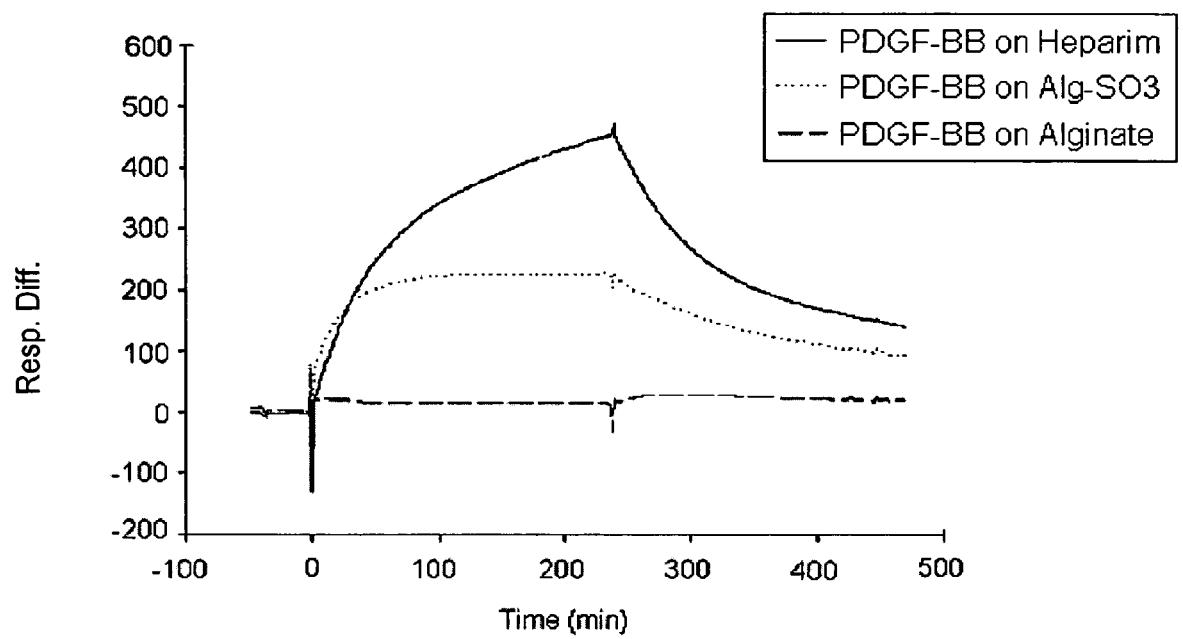
FIGS. 2A-2B show SPR sensorgrams of PDGF-BB binding to alginate sulfate, over a range of peptide concentrations. (2A) PDGF-BB (400 nM) binding to heparin, alginate sulfate and alginate immobilized on sensor chip SA. Binding was specific for heparin and alginate sulfate, while no interactions with immobilized biotinylated alginate were seen. (2B) PDGF-BB was injected over immobilized alginate sulfate. The SPR sensorgram presents the affinity profile as a function of PDGF-BB concentrations.
Figure 2B:
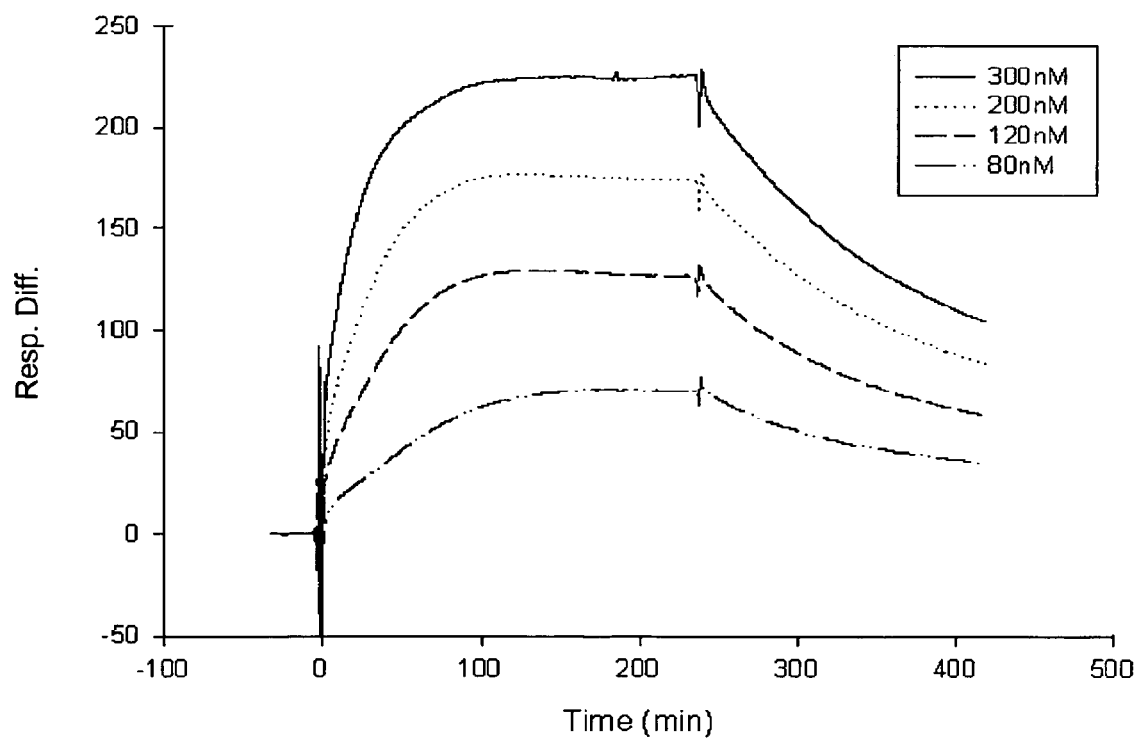
Figure 3A:
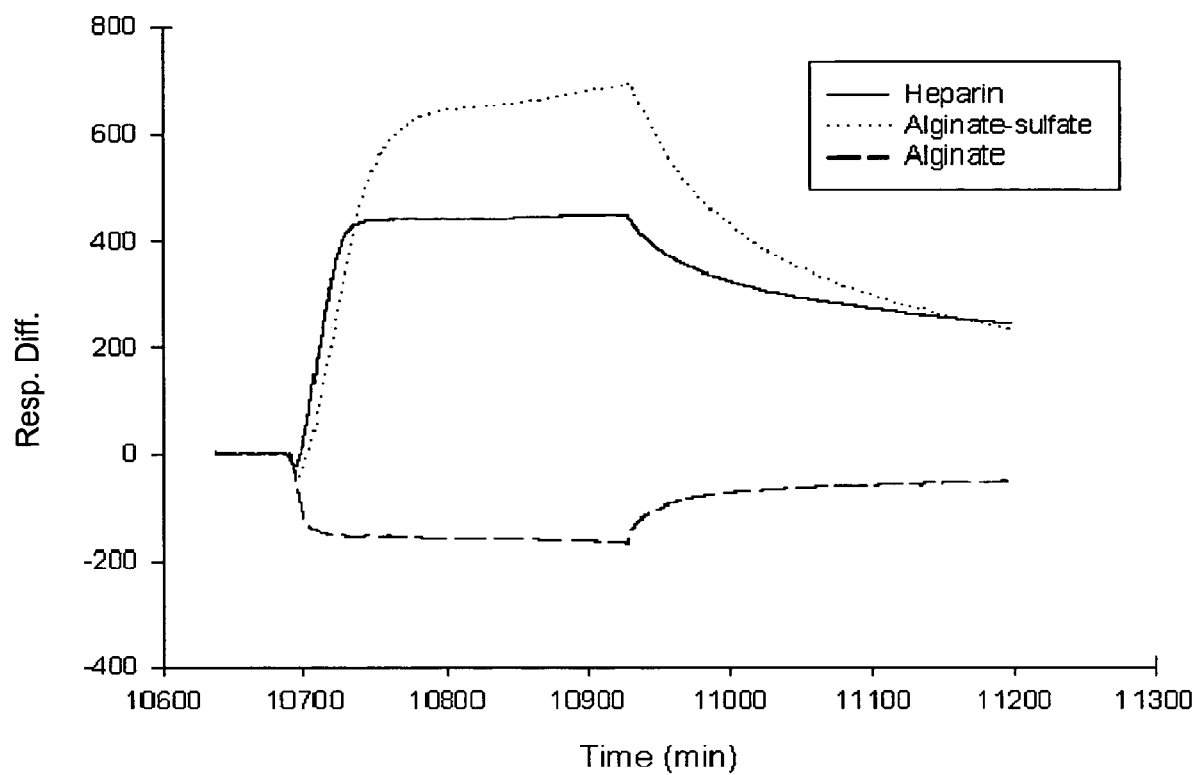
FIGS. 3A-3B show SPR sensorgrams of bFGF binding to alginate sulfate, over a range of peptide concentrations. (3A) bFGF (1 μM) binding to heparin, alginate sulfate and alginate immobilized on sensor chip SA. Binding was specific for heparin and alginate sulfate while no interactions with immobilized biotinylated alginate were seen. (3B) bFGF was injected over immobilized alginate sulfate on sensor chip SA. SPR sensorgram presents the affinity profile as a function of bFGF concentrations (Table 2).
Figure 3B:
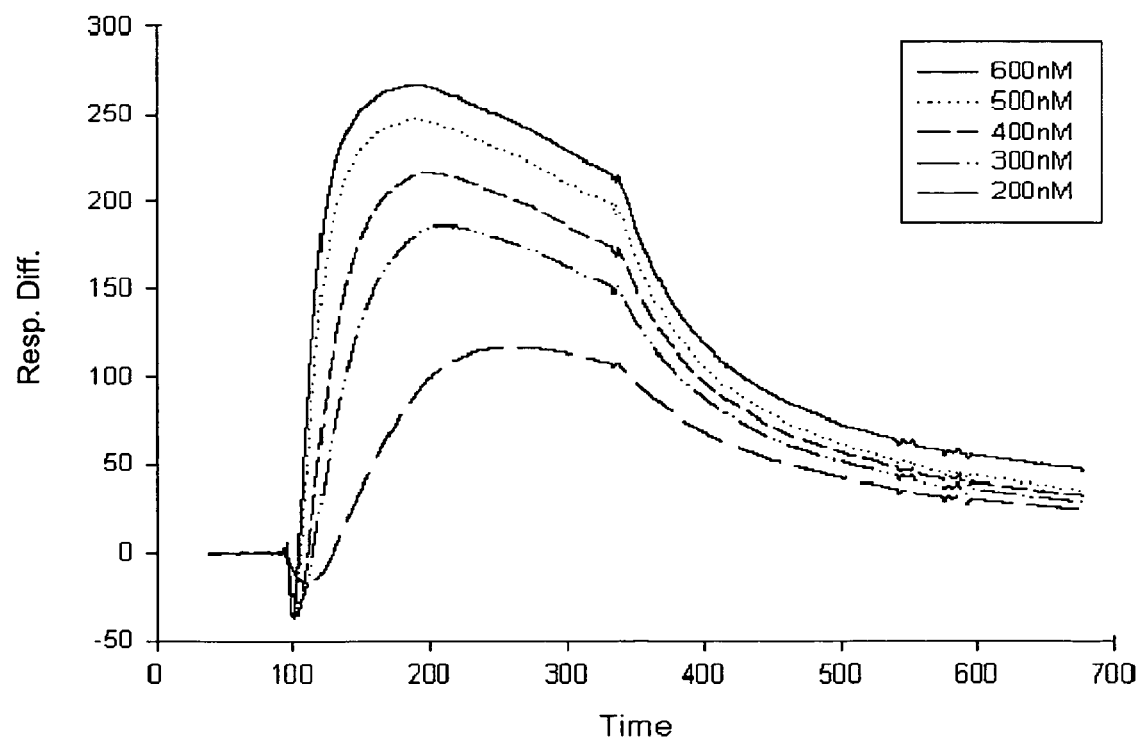
Figure 4A:
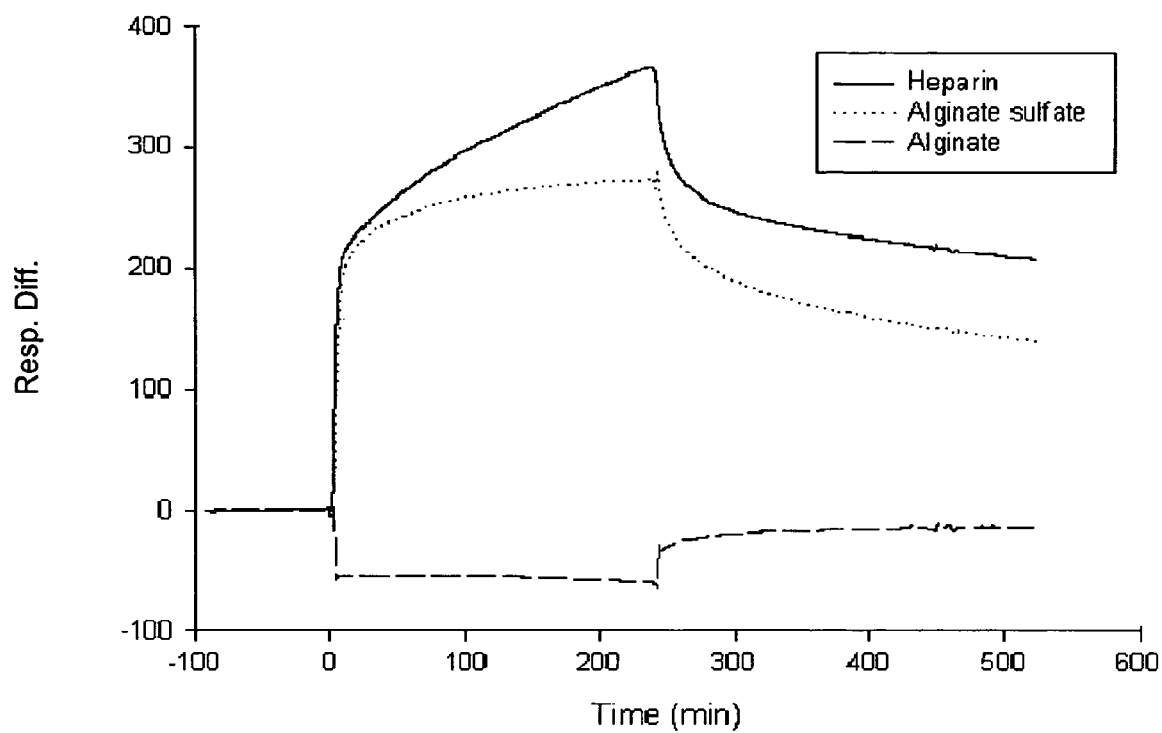
FIGS. 4A-4B show SPR sensorgrams of VEGF binding to alginate sulfate, over a range of peptide concentrations. (4A) VEGF (5 μM) binding to heparin, alginate sulfate and alginate immobilized on sensor chip SA. Binding was specific for heparin and alginate sulfate while no interactions with immobilized biotinylated alginate were seen. (4B) VEGF was injected over immobilized alginate sulfate on sensor chip SA. SPR sensorgram presents the affinity profile as a function of VEGF concentrations
Figure 4B:
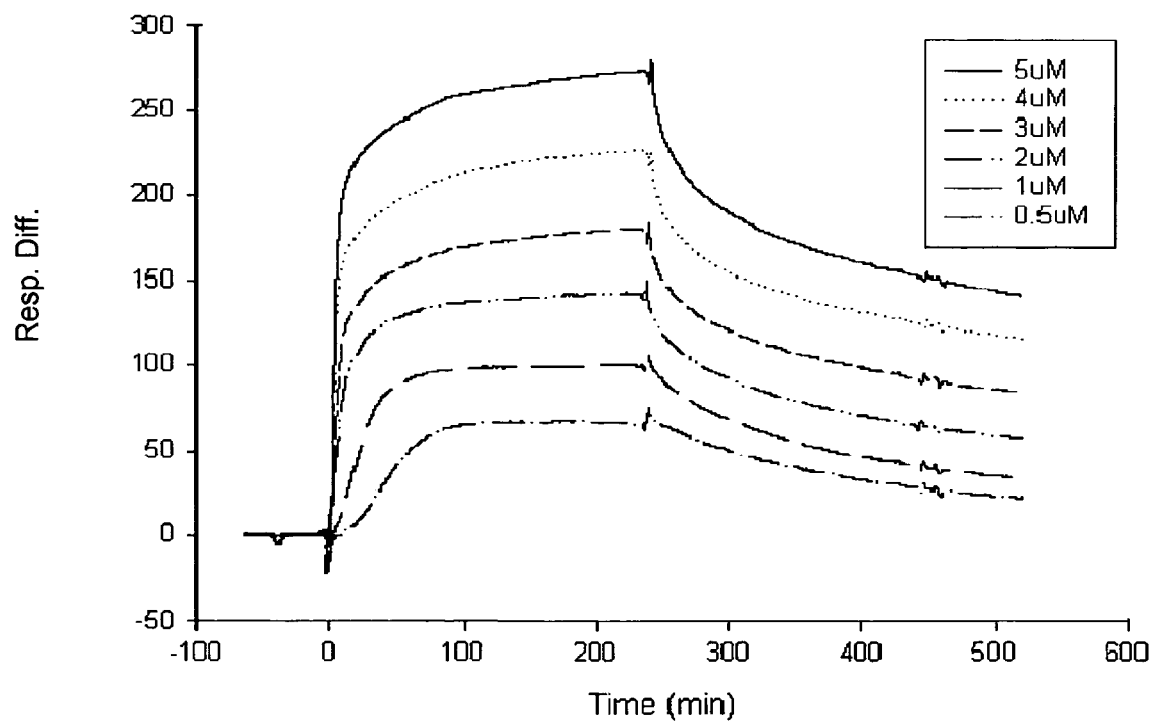
Figure 5A:
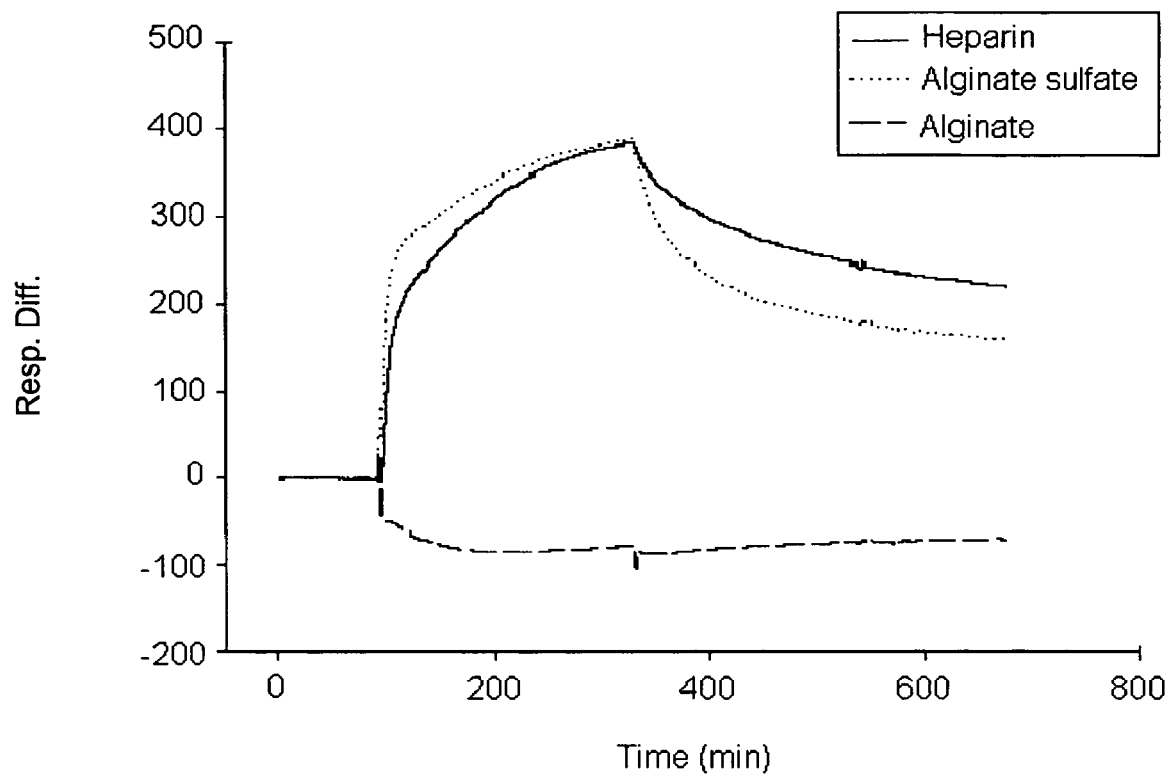
FIGS. 5A-5B show SPR sensorgrams of TGFβ1 binding to alginate sulfate, over a range of peptide concentrations. (5A) TGFβ1 (300 nM) binding to heparin, alginate sulfate and alginate immobilized on sensor chip SA. Binding was specific for heparin and alginate sulfate while no interactions with immobilized biotinylated alginate were seen. (5B) TGFβ1 was injected over immobilized alginate sulfate on sensor chip SA. SPR sensorgram presents the affinity profile as a function of TGFβ1 concentrations.
Figure 5B:
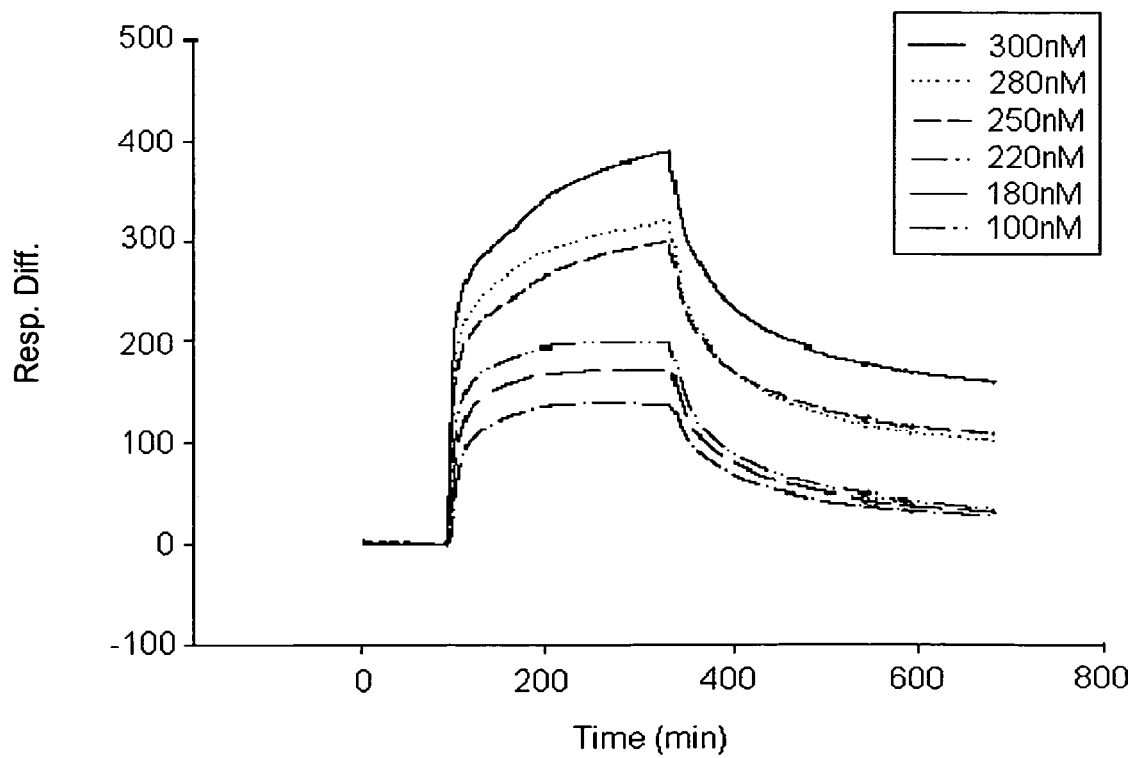
Figure 6A:
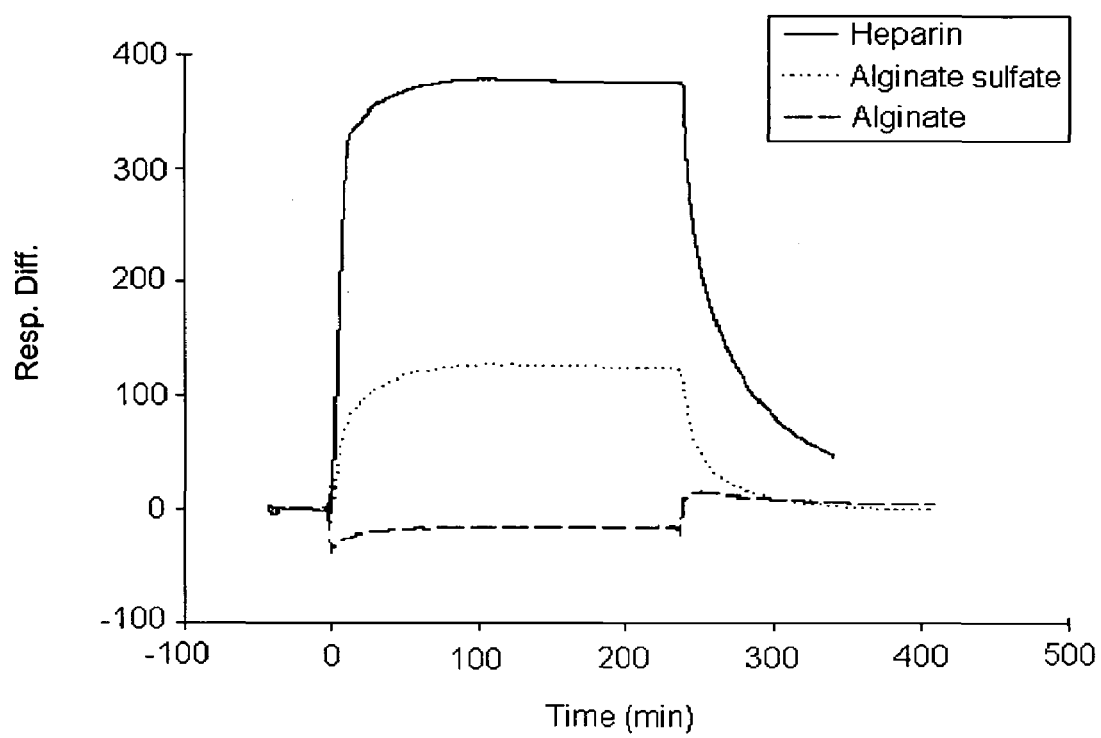
FIGS. 6A-6B show SPR sensorgrams of aFGF binding to alginate sulfate, over a range of peptide concentrations. (6A) aFGF (200 nM) binding to heparin, alginate sulfate and alginate immobilized on sensor chip SA. Binding was specific for heparin and alginate sulfate while no interactions with immobilized biotinylated alginate were seen. (6B) aFGF was injected over immobilized alginate sulfate on sensor chip SA. SPR sensorgram presents the affinity profile as a function of aFGF concentrations
Figure 6B:
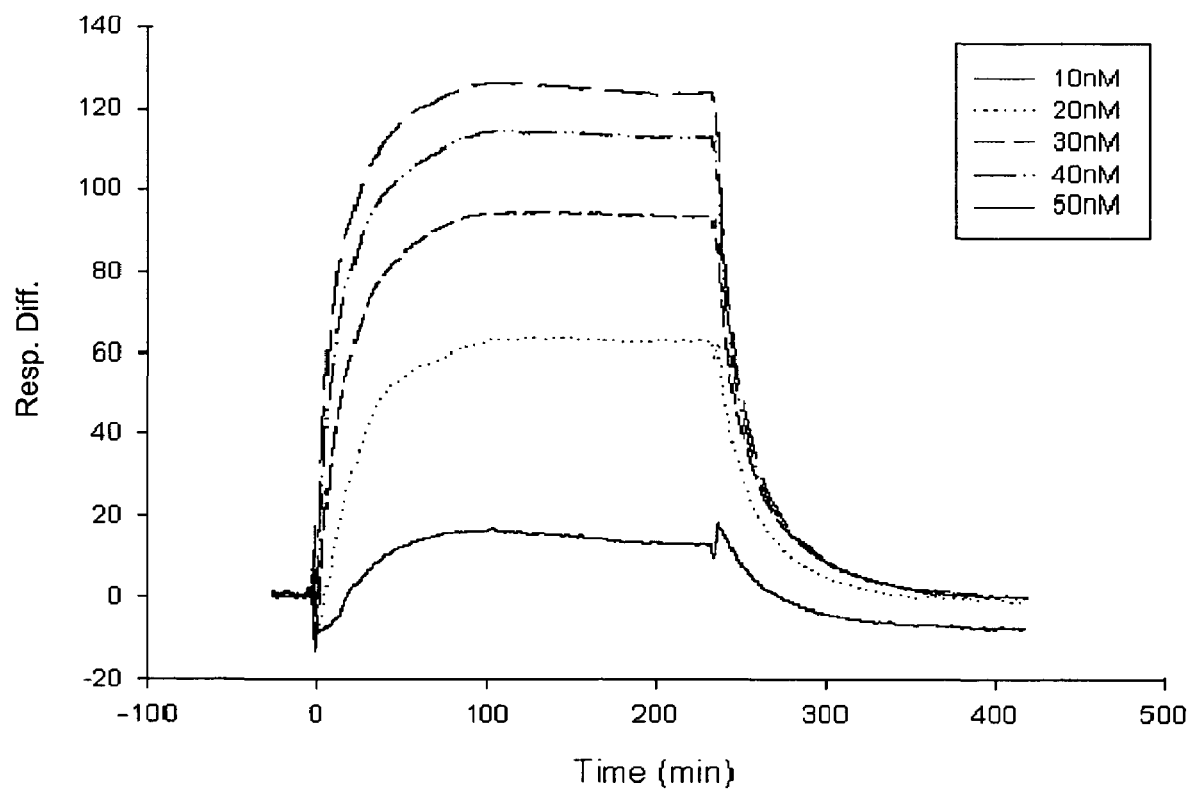
Figure 7A:
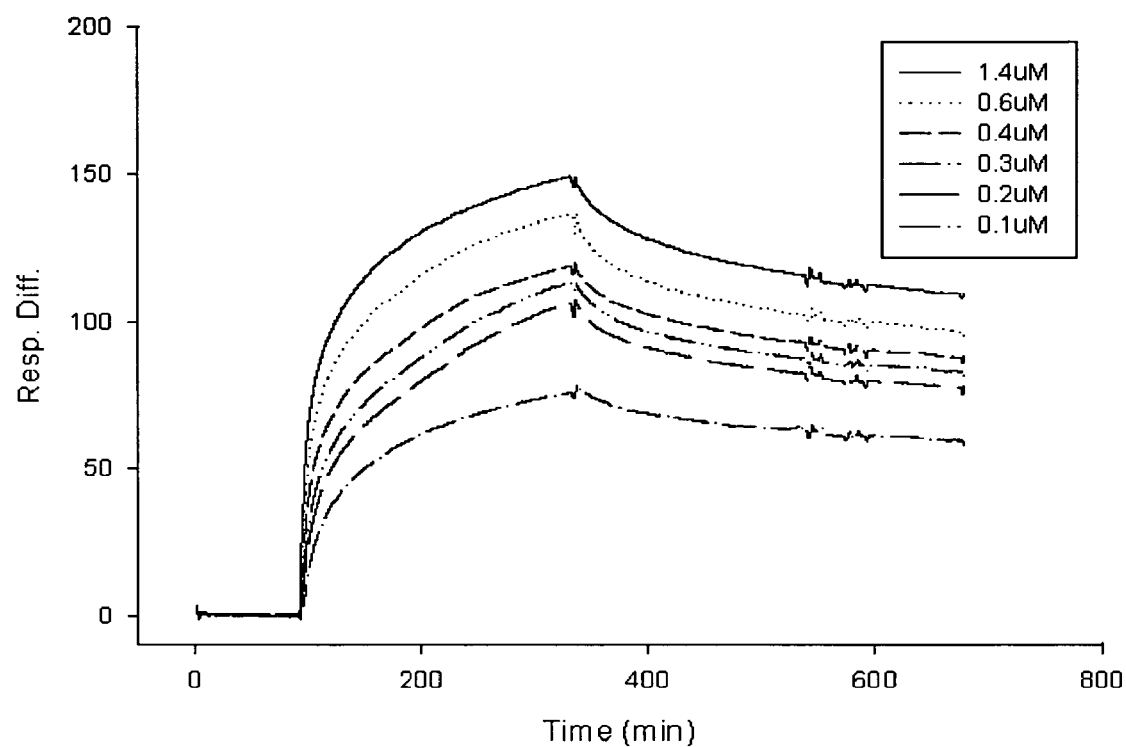
FIGS. 7A-7B show SPR sensorgrams of IL-6 binding to alginate sulfate, over a range of peptide concentrations. (7A) IL-6 (1.4 µM) binding to heparin, alginate sulfate and alginate immobilized on sensor chip SA. Binding was specific for heparin and alginate sulfate while no interactions with immobilized biotinylated alginate were seen. (7B) IL-6 was injected over immobilized alginate sulfate on sensor chip SA. SPR sensorgram presents the affinity profile as a function of IL-6 concentrations.
Figure 7B:
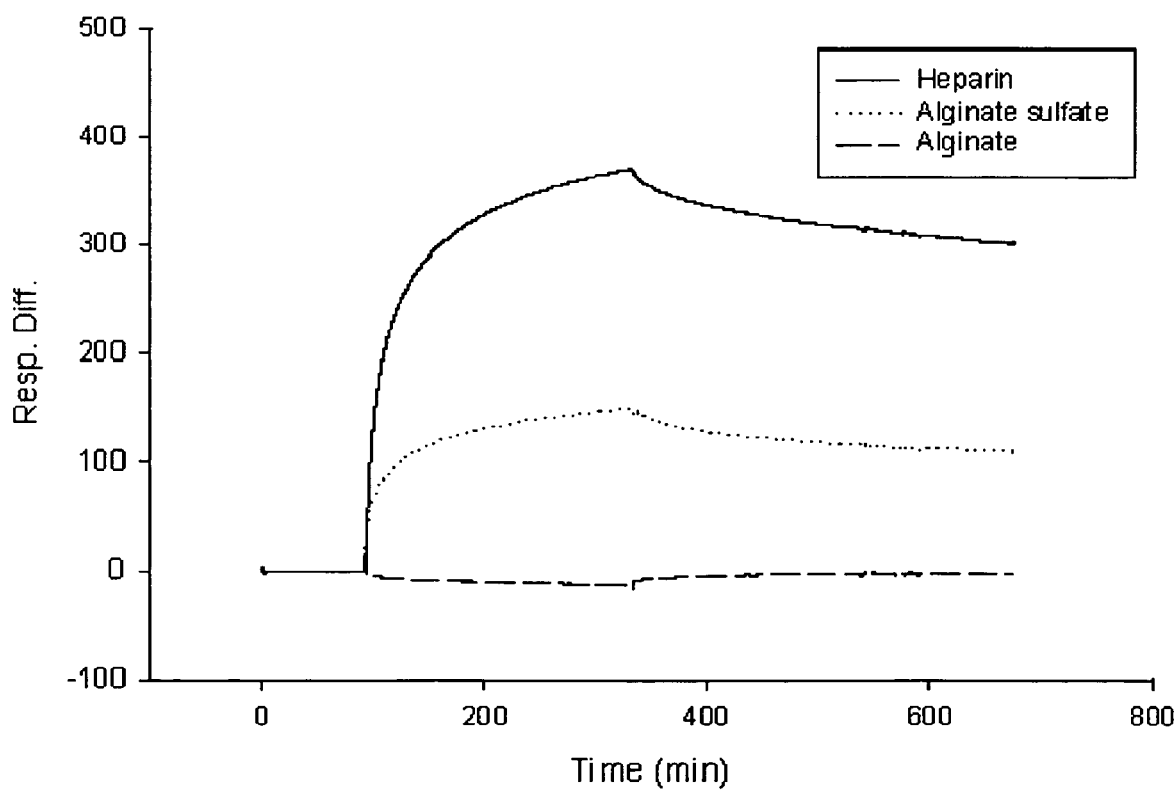
Figure 8A:
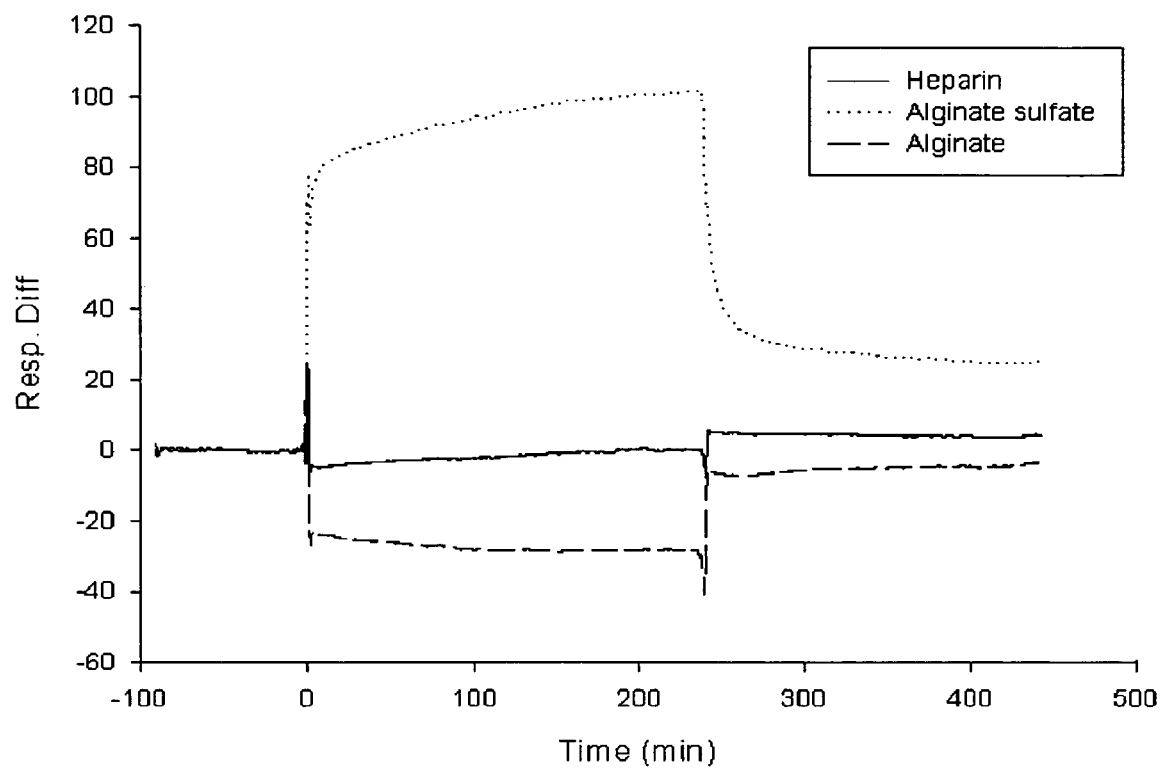
FIGS. 8A-8B show SPR sensorgrams of TPO binding to alginate sulfate, over a range of peptide concentrations. (8A) TPO (1.0 µM) binding to heparin, alginate sulfate and alginate immobilized on sensor chip SA. Binding was specific for heparin and alginate sulfate while no interactions with immobilized biotinylated alginate were seen. (8B) TPO was injected over immobilized alginate sulfate on sensor chip SA. SPR sensorgram presents the affinity profile as a function of TPO concentrations.
Figure 8B:
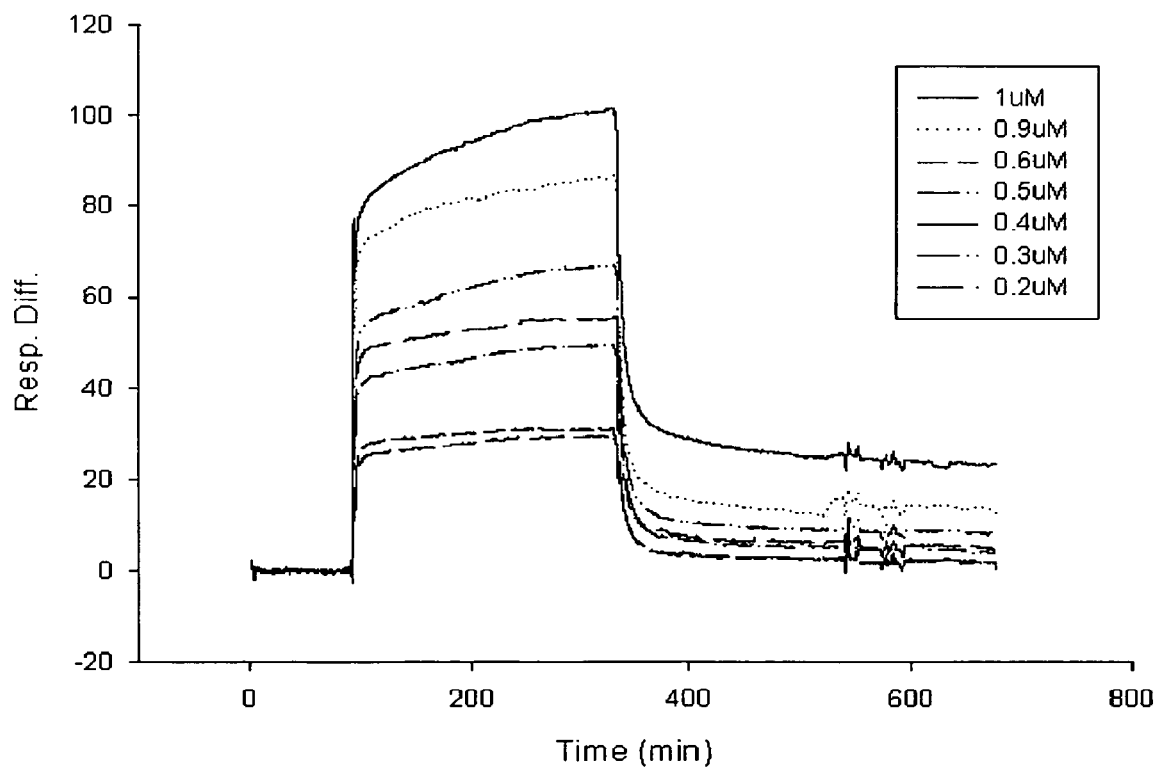
Figure 9A:
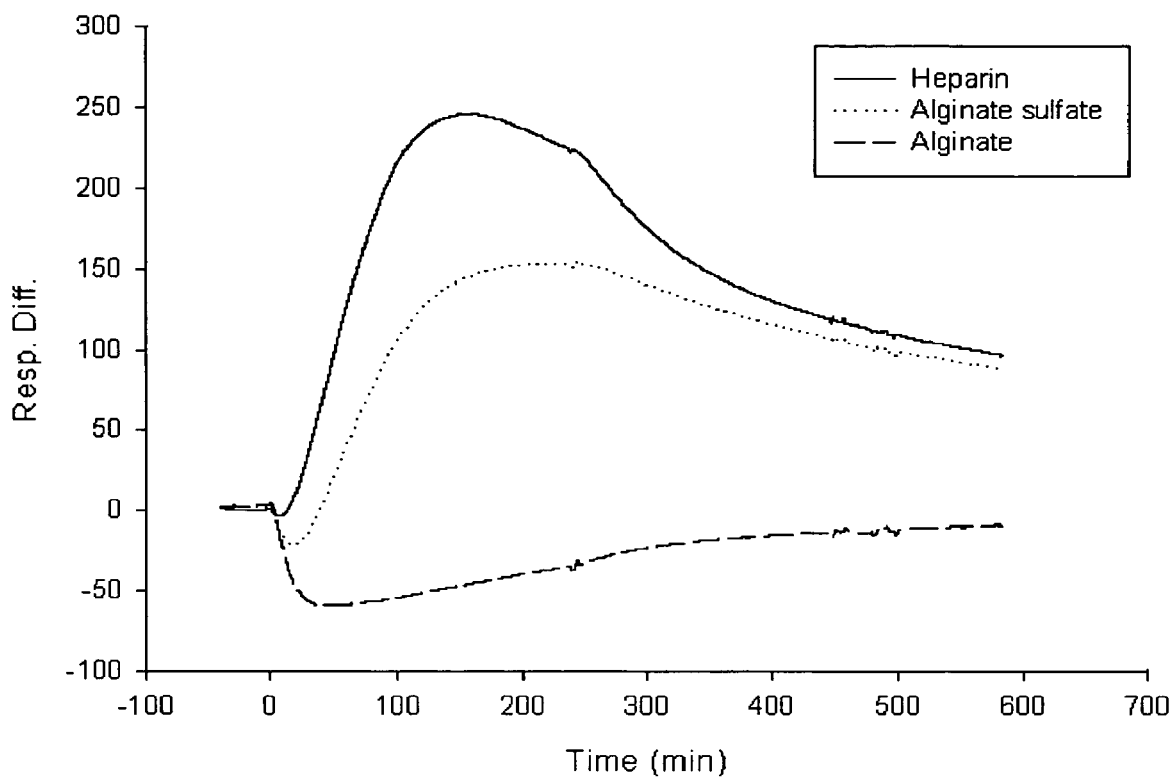
FIGS. 9A-9B show SPR sensorgrams of SDF-1 binding to alginate sulfate, over a range of peptide concentrations. (9A) SDF-1 (600 nM) binding to heparin, alginate sulfate and alginate immobilized on sensor chip SA. Binding was specific for heparin and alginate sulfate while no interactions with immobilized biotinylated alginate were seen. (9B) SDF-1 was injected over immobilized alginate sulfate on sensor chip SA. SPR sensorgram presents the affinity profile as a function of SDF-1 concentrations.
Figure 9B:
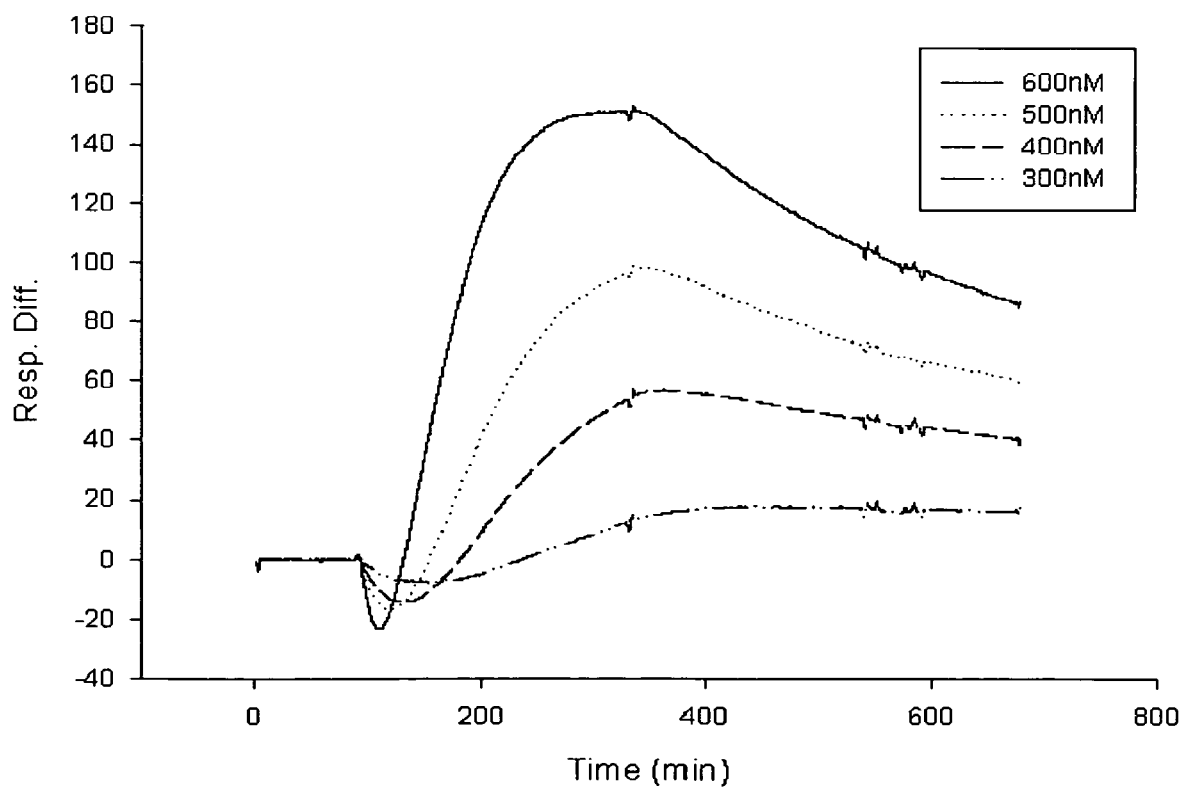
Figure 10A:
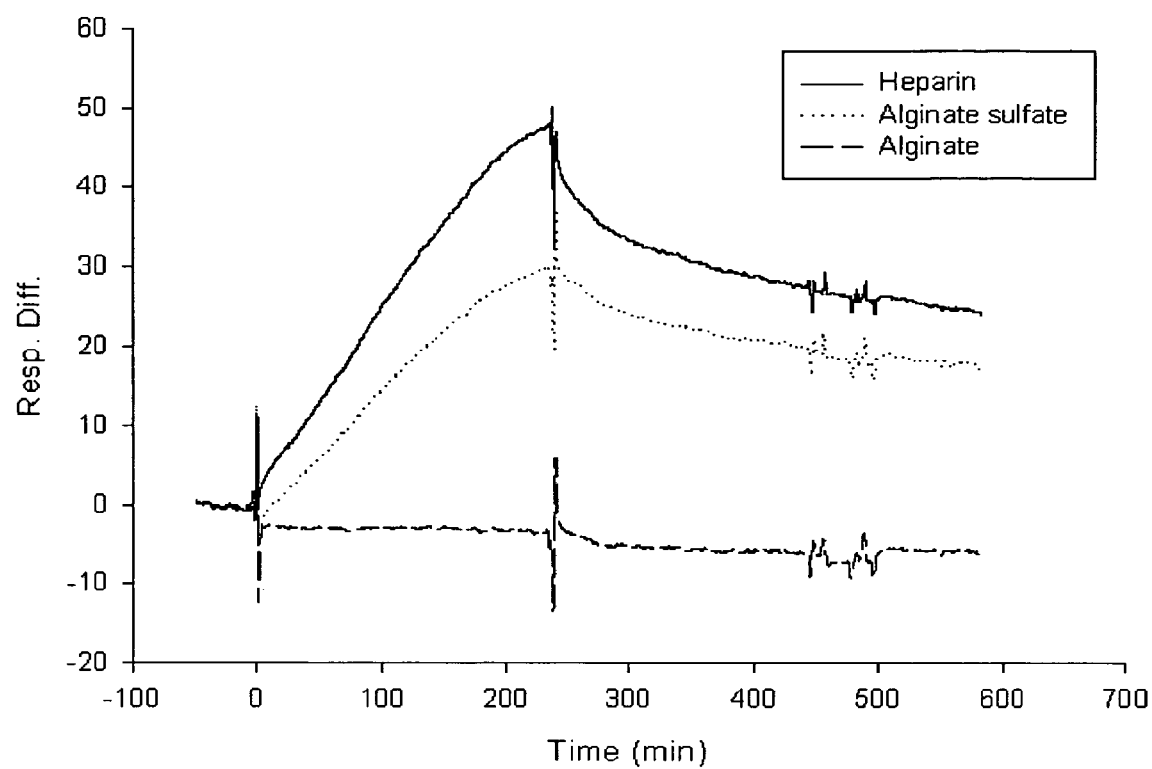
FIGS. 10A-10B show SPR sensorgrams of HGF binding to alginate sulfate, over a range of peptide concentrations. (10A) HGF (250 nM) binding to heparin, alginate sulfate and alginate immobilized on sensor chip SA. Binding was specific for heparin and alginate sulfate while no interactions with immobilized biotinylated alginate were seen. (10B) HGF was injected over immobilized alginate sulfate on sensor chip SA. SPR sensorgram presents the affinity profile as a function of HGF concentrations.
Figure 10B:
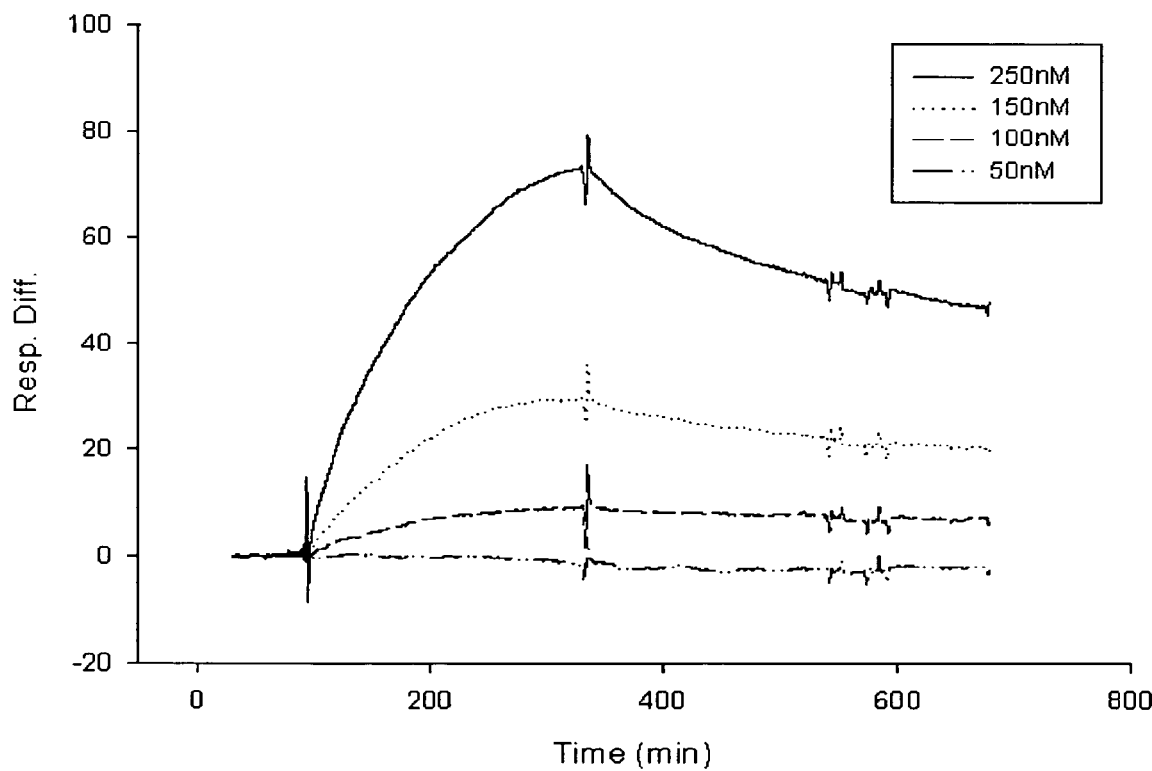
Figure 11A:
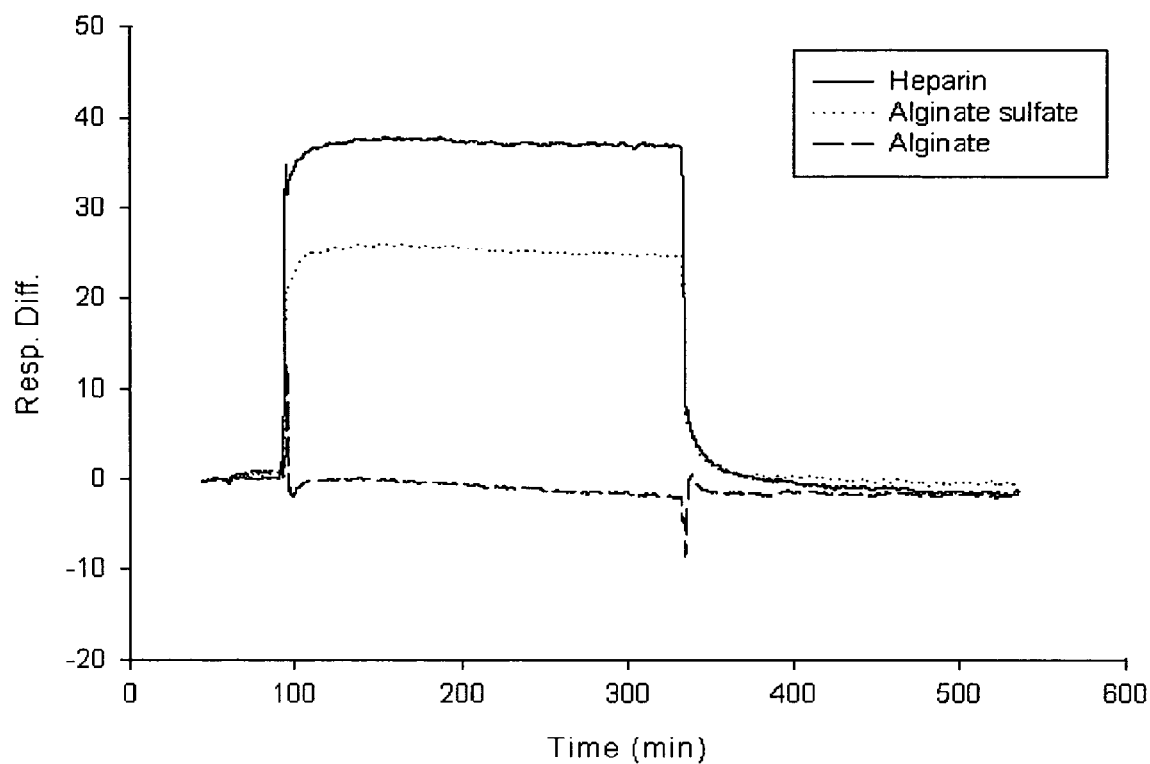
FIGS. 11A-11B show SPR sensorgrams of EGF binding to alginate sulfate, over a range of peptide concentrations. (11A) EGF (5 µM) binding to heparin, alginate sulfate and alginate immobilized on sensor chip SA. Binding was specific for heparin and alginate sulfate while no interactions with immobilized biotinylated alginate were seen. (11B) EGF was injected over immobilized alginate sulfate on sensor chip SA. SPR sensorgram presents the affinity profile as a function of EGF concentrations.
Figure 11B:
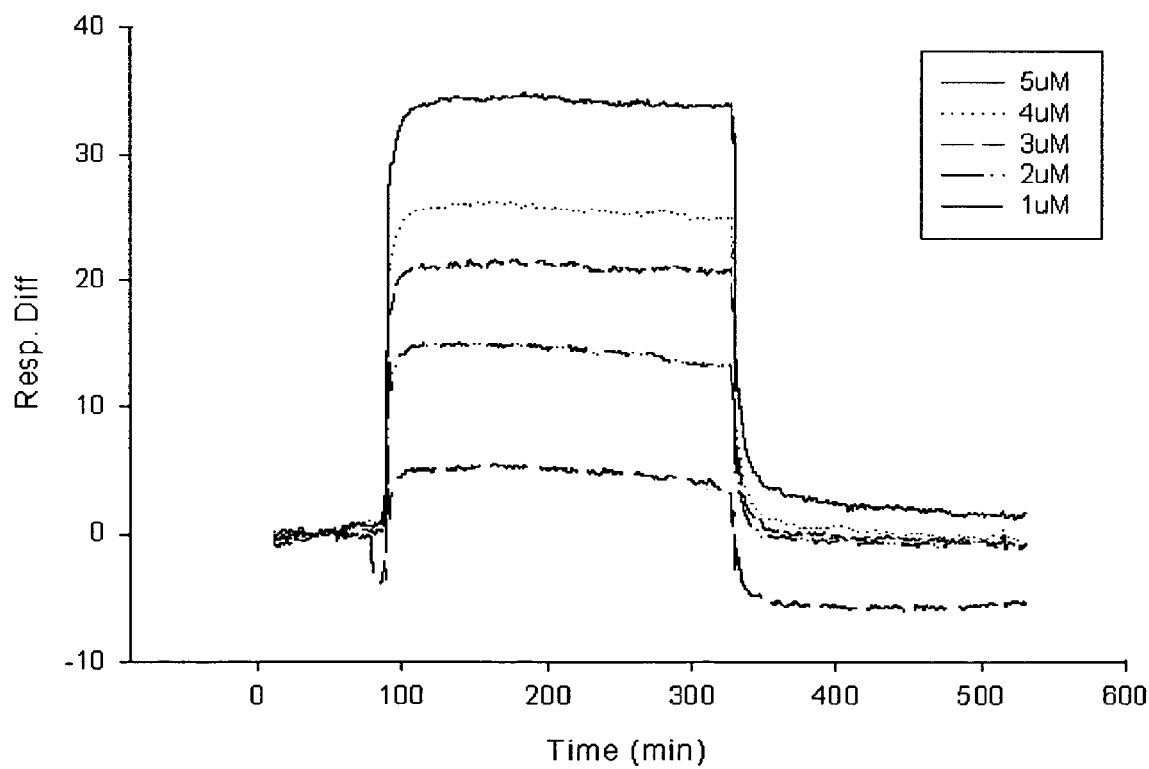
Figure 12A:
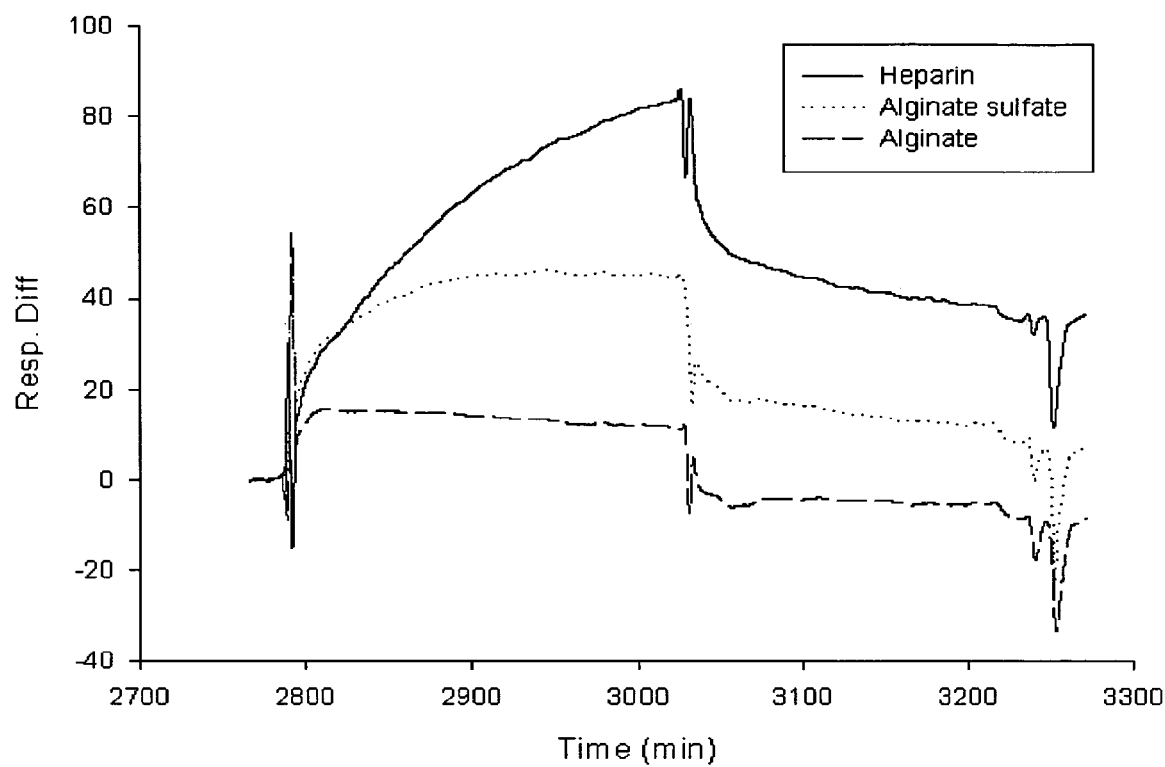
FIGS. 12A-12B show SPR sensorgrams of IGF binding to alginate sulfate, over a range of peptide concentrations. (12A) IGF (5 µM) binding to heparin, alginate sulfate and alginate immobilized on sensor chip SA. Binding was specific for heparin and alginate sulfate while no interactions with immobilized biotinylated alginate were seen. (12B) IGF was injected over immobilized alginate sulfate on sensor chip SA. SPR sensorgram presents the affinity profile as a function of IGF concentrations.
Figure 12B:
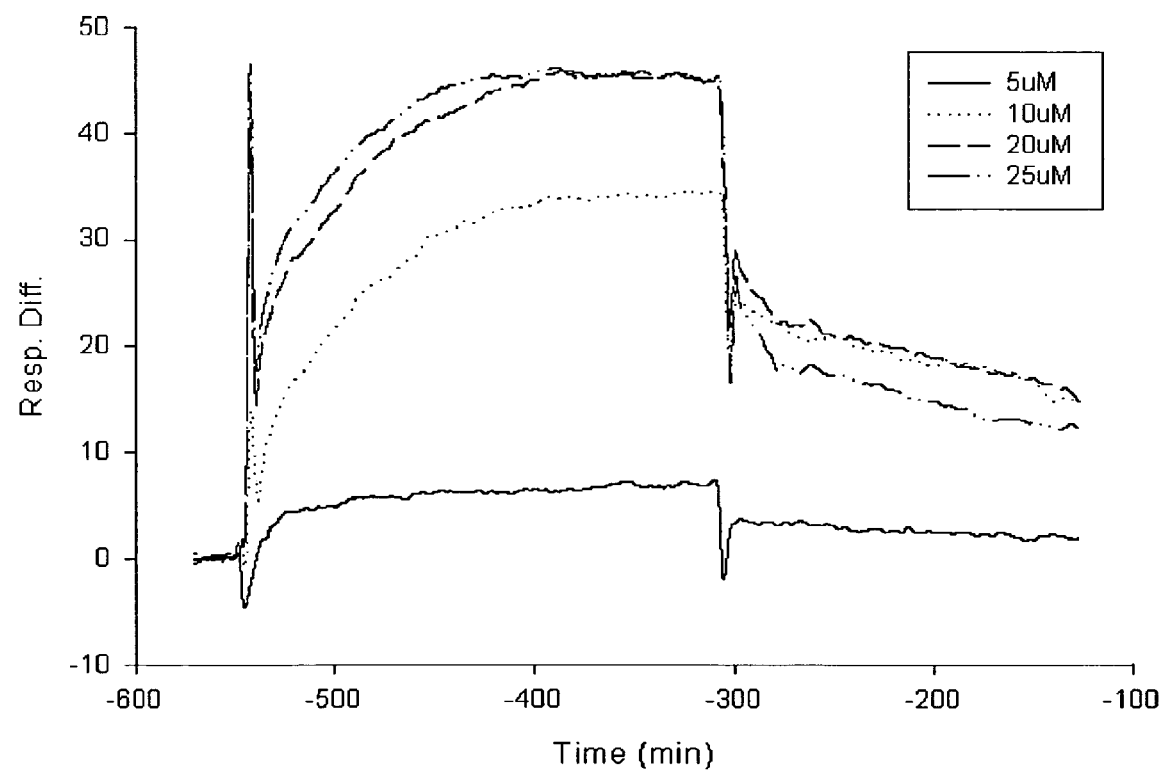
Figure 13:
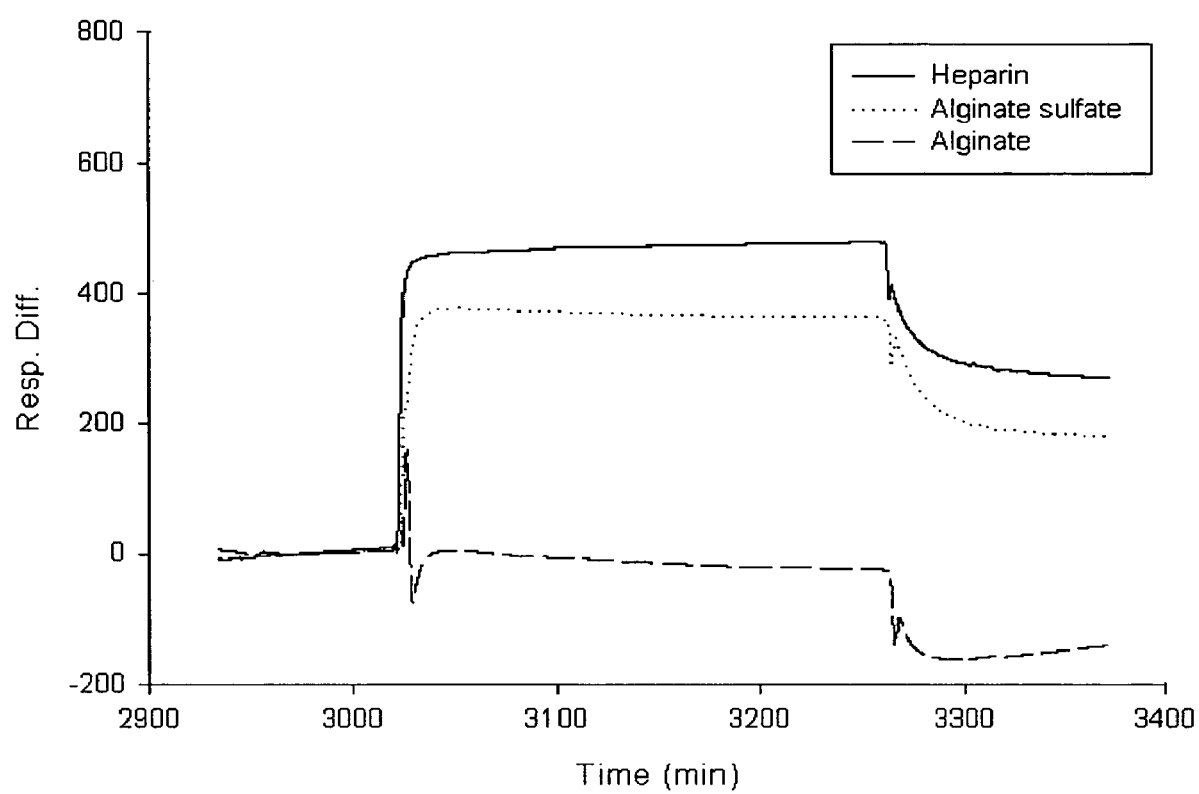
FIG. 13 shows PDGF-AA (550 nM) binding to heparin, alginate sulfate and alginate immobilized on sensor chip SA. Binding was specific for heparin and alginate sulfate while no interactions with immobilized biotinylated alginate were seen.

The present invention relates, in one aspect, to a bioconjugate comprising a sulfated polysaccharide and at least one bioactive polypeptide capable of binding a sulfate group of said sulfated polysaccharide. These bioconjugates are useful when administered to a mammal, for sustained release of said bioactive peptide(s) from said bioconjugate.

The at least one bioactive polypeptide may be a positively charged polypeptide, a heparin-binding polypeptide, or both.

The term "bioactive polypeptide" as used herein refers to a polypeptide exhibiting a variety of pharmacological activities in vivo, and include but are not limited to, growth factors, cytokines, chemokines, angiogenic factors, immunomodulators, hormones, and the like.

In the present application, the terms "polypeptide" and "proteins" are used interchangeably.

The term "positively charged polypeptides" refers to a polypeptide/protein that has a positive net charge at physiological pH of about pH=7.5. Examples of positively charged proteins include, but are not limited to, insulin, glatiramer acetate, antithrombin III, interferon γ (also known as heparin-binding protein), IGF, somatostatin, erythropoietin, luteinizing hormone-releasing hormone (LH-RH) and interleukins such as IL-2 and IL-6.

The term "heparin-binding protein or polypeptide" refers to proteins that have clusters of positively-charged basic amino acids and form ion pairs with specially defined negatively-charged sulfo or carboxyl groups on the heparin chain (See Capila and Linhardt, 2002). Examples of heparin-binding proteins include, but are not limited to, thrombopoietin (TPO); proteases/esterases such as antithrombin III (AT III), serine protease inhibitor (SLP1), C1 esterase inhibitor (C1 INH) and Vaccinia virus complement control protein (VCP); growth factors such as a fibroblast growth factor (FGF, aFGF or bFGF), a FGF receptor, vascular endothelial growth factor (VEGF), insulin-like growth factor (IGF), hepatocyte growth factor (HGF), transforming growth factor β1 (TGF-β1), a platelet-derived growth factor (PDGF, PDGF-AA and PDGF-BB), and epidermal growth factor (EGF); chemokines such as platelet factor 4 (PF-4, now called CXC chemokine ligand 4 or CXCL4), stromal cell-derived factor-1 (SDF-1), IL-6, IL-8, RANTES (Regulated on Activation, Normal T Expressed and Secreted), monocyte chemoattractant protein-1 (MCP-1), macrophage inflammatory peptide-1 (MIP-1), lymphotactin, and fractalkine; lipid or membrane-binding proteins such as an annexin, apolipoprotein E (ApoE); pathogen proteins such as human immunodeficiency virus type-1 (HIV-1) coat proteins e.g. HIV-1 gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA; and adhesion proteins such as 1- and P-selectin, heparin-binding growth-associated molecule (HB-GAM), thrombospondin type I repeat (TSR), and amyloid P (AP).

In preferred embodiments of the present invention, the at last one heparin-binding polypeptide is selected from the group consisting of PDGF-BB, PDGF-AA, bFGF, aFGF, VEGF, TGFβ1, IL-6, TPO, SDF-1, HGF, EGF and IGF.

In a preferred embodiment of the invention, the at least one bioactive polypeptide is an angiogenic factor or a growth factor exhibiting angiogenic activity selected from the group consisting of TGF-β1, VEGF, bFGF, aFGF, PDGF-BB, IGF, and a combination thereof.

In a more preferred embodiment of the invention, said at least one angiogenic factor consists of bFGF.

In yet another more preferred embodiment of the invention, the bioconjugate comprises a combination of VEGF, PDGF-BB and TGF-β1.

In accordance with the present invention, the sulfated polysaccharides forming the bioconjugate may be composed of different recurring monosaccharide units, may be of different lengths, and may have different types of bonds linking said units. The sulfated polysaccharides may be linear as sulfated cellulose branched as sulfated glycogen, and may vary in length, for example, it may be as small as a sulfated trisaccharide. The sulfated polysaccharide may be a homopolysaccharide including, but not limited to, starch, glycogen, cellulose or chitin or a heteropolysaccharide including, but not limited to, alginic acid (alginate) salts and hyaluronic acid.

In a preferred embodiment of the invention, the polysaccharide comprises uronic acid residues such D-glucoronic, D-galacturonic, D-mannuronic, L-iduronic, and L-guluronic acids. Example of polysaccharides comprising uronic acid include, but are not limited to, alginic acid salts, preferably sodium alginate, pectin, gums and mucilages from plant sources; and glycosaminoglycans (GAGs) from animal sources including hyaluronic acid (hyaluronan). The sulfated polysaecharides comprising uronic acid can be chemically sulfated or may be naturally sulfated polysaccharides.

In one preferred embodiment of the present invention, the sulfated polysaccharide in the bioconjugate is alginate sulfate. In another embodiment the sulfated polysaccharide is hyaluronan sulfate.

Alginic acid is a linear polysaccharide obtained from brown algae and seaweed and consist of β-1,4-linked glucuronic and mannuronic acid units.

Hyaluronic acid is composed of repeating dimmeric units of glucuronic acid and N-acetyl glucosamine and forms the core complex proteoglycans aggregates found in the extracellular matrix.

In a more preferred embodiment the bioconjugate is selected from the group consisting of aFGF-alginate sulfate, bFGF-alginate sulfate, PDGF-BB-alginate sulfate, PDGF-AA-alginate sulfate, VEGF-alginate sulfate, TGFβ1-alginate sulfate, IL-6-alginate sulfate, TPO-alginate sulfate, SDF-1-alginate sulfate, HGF-alginate sulfate, EGF-alginate sulfate, IGF-alginate sulfate, bFGF-hyaluronan sulfate and VEGF-hyaluronan sulfate.

The present invention is based on results obtained with the sulfated polysaccharides alginate sulfate and sulfated hyaluronan. We show herein that alginate and hyaluronic are sulfated and converted into reactive polymers capable of specifically interacting with at least one positively-charged polypeptide and/or heparin-binding polypeptide, forming a bioconjugate capable of sustaining the release of said at least one polypeptide. By sulfating the polysaccharides, we endowed them with properties which allowed binding and controlled release of important signal proteins such as various cytokines and growth factors. Alginate sulfate and hyaluronan sulfate were both found to mimic the biological specificities of heparan sulfate and heparin when forming the bioconjugates.

We prepared sulfated alginate and hyaluronan with different sulfation degrees and showed, by SPR technology, the interaction of the alginate sulfate and hyaluronan sulfate with various bioactive polypeptides. We determined that various positively-charged proteins and heparin-binding proteins bound specifically to the sulfated alginates and the sulfated hyaluronans with particular affinity-binding constants. Said proteins bound alginate sulfate and hyaluronan sulfate with high affinity and some of them exhibited superior binding to alginate sulfate and hyaluronan sulfate than to heparin (see, for example, bFGF, SDF-1, TGFβ1, and PDGF-BB binding in Table 3 hereinafter). We found that the pattern and kinetics of release of positively-charged proteins and heparin-binding proteins from these bioconjugates are dependent on the relative affinity of said proteins to the sulfated polysaccharide.

A bioconjugate according to the present invention can be injected to any part of the human body and serve as a delivery system for said bioactive polypeptide(s), for example, we show herein that administration of a bioconjugate comprising sulfated alginate and bFGF or a mixture of the three angiogenic factors, VEGF, TGF-b1 and PDGF-BB to animals, promoted sustained release of the factors and lead to superior vascularization and more mature blood vessels than the same factors supplied with non-modified alginate. The experiment with the three angiogenic factors demonstrate that the angiogenic factors work in a complementary and coordinated manner to form mature and high density blood vessels.

Thus in one aspect, the invention provides a pharmaceutical composition comprising a bioconjugate according to the invention and a pharmaceutically acceptable carrier.

In a preferred embodiment, the invention provides a pharmaceutical composition as a delivery system for sustained release of at least one bioactive polypeptide, comprising a bioconjugate composed of said at least one bioactive polypeptide and a sulfated polysaccharide, wherein said bioactive polypeptide is capable of binding a sulfate group of said sulfated polysaccharide.

For its use as a delivery system for the sustained release of the bioactive polypeptide(s), the bioconjugate of the invention may be injected or implanted in a mammal, optionally in association with or provided in a supporting matrix, used as scaffold for cell transplantation and tissue engineering. In the examples below, we show the successful sustained release of bioactive peptides from the bioconjugate of the invention present in capsules or in scaffolds formed by alginate.

Thus, in a preferred embodiment of the invention, the pharmaceutical composition further comprises a supporting matrix.

The matrix may serve as support or as a carrier for the bioconjugate and may be made up of particles or porous materials. The matrix material may be flexible and amenable to be fixed in place preventing its migration to an unintended location. The polymer matrix materials can be either natural or synthetic and include, but are not limited to, synthetic polymers such as polyethylene glycol (polyethylene oxide), poly(vinyl alcohol), polylactic acid, polyglycolic acid, and polyhydroxybutyrate, or natural polymers like collagen, fibrin, and gelatin, or polysaccharides like chitosan and alginate.

The matrix material is preferably biodegradable. Thus, physical removal of the matrix material from recipient's tissue following drug delivery is not necessary and there is no concern about effects of the residual matrix in the long term. Of advantage is the use of a matrix material which does not provoke a significant inflammatory or proliferative tissue response or which does not alter or interfere with the recipient's natural defense systems and healing processes.

The matrix may be in any form appropriate to the mode of delivery, for example, hydrogel, beads, microspheres (microbeads), hydrogel microcapsules, sponges, scaffolds, foams, colloidal dispersions, suspensions, and the like. Thus, a sustained release dosage form based on bioconjugates of sulfated polysaccharides and bioactive peptides may be fashioned as liquids, meshes, sponges, fibers and hydrogels.

In certain embodiments of the invention, the supporting matrix is selected from the group consisting of a polysaccharide, a protein, an extracellular matrix component a synthetic polymer and a mixture thereof.

In one preferred embodiment of the invention, the supporting matrix consists of polysaccharide, preferably of alginate hydrogel or hyaluronan hydrogel.

The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1,3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, creams, lotions, gels, foams, mousses, sprays and the like. Methodology and components for formulation of pharmaceutical compositions are well known and can be found, for example, in Remington's Pharmaceutical Sciences, Eighteenth Edition, A. R. Gennaro, Ed., Mack Publishing Co. Easton Pa., 1990.

In one embodiment of the invention the carrier consists of an aqueous buffer.

In another embodiment of the invention, the carrier consists of a polysaccharide, and is preferably alginate hydrogel or hyaluronic acid.

The composition can be administered to a patient in need thereof in a variety of ways. The routes of administration include but are not limited to intraliver, intradermal, transdermal (e.g. in slow release formulations), intramuscular, intraperitoneal, intravenous, intracoronary, subcutaneous, oral, epidural, topical, and intranasal routes. Any other therapeutically efficacious route of administration can be used.

In a further aspect, the invention provides a method for the sustained released administration of at least one bioactive polypeptide which is capable of binding a sulfate group of a sulfated polysaccharide to a patient in need of treatment with said polypeptide, wherein the method comprises administering to said patient an effective amount of a bioconjugate of the invention comprising a sulfated polysaccharide and at least one bioactive polypeptide capable of binding a sulfate group of said sulfated polysaccharide.

Cochran et al. (J. Med. Chem. 2003, 46, 4601-4608) studied the binding interactions of the anticancer agent PI-88 and derivatives of PI-88 with the angiogenic factors FGF-1, FGF-2 and VEGF. PI-88 is a mixture of highly sulfated, monophosphorylated mannose oligosaccharide ranging in size from di- to hexasaccharide. The derivatives of the PI-88 which were studied had defined carbohydrate chain length (2 to 5 saccharide units) and were lacking a phosphate group. The results obtained in this binding study indicated that the two dominant components of the PI-88 mixture, namely, the penta- and tetrasaccharide components, have increased affinity for the angiogenic factors and therefore are responsible for the bulk of the antiangiogenic activity of PI-88. The binding studies demonstrated that PI-88 had greater affinity for FGF-1 and VEGF than heparin, heparan sulfate or polyanionic drugs such as sucrose octasulfate. The binding was highly dependent on the degree of sulfation and the chain length tested.

Alginate and hyaluronan are polysaccharides and not short oligosaccharide as PI-88, and are of different composition than PI-88. It was thus unexpected that their sulfated form would exhibit high affinity for angiogenic factors and in general for heparin-binding polypeptides and/or positively-charged bioactive polypeptides. Moreover, we found that alginate sulfate and hyaluronan bound bFGF, SDF-1, TGFβ1, and PDGF-BB with higher affinity than heparin (Tables 3 and 6).

In view of the high affinity of alginate sulfate and hyaluronan sulfate to the bioactive polypeptides capable of binding sulfated polysaccharides, said sulfated polysaccharides themselves may be exploited for the elimination of said bioactive polypeptides in diseases or disorders caused by or associated with the activity of said bioactive polypeptides, for example, alginate sulfate or sulfated hyaluronan can be used for the treatment of: cancer which is known to be associated with growth factors and angiogenic factors; inflammatory diseases such as rheumatoid arthritis and bowel inflammatory diseases (e.g. Crohn's disease) associated with IL-6 activity; proliferative diabetic retinopathy associated with VEGF activity; myelodysplastic syndrome with myelofibrosis associated with TGFb and TPO activity; diabetic peripheral neuropathy associated with IFG activity; pulmonary arterial hypertension associated with PDGF-BB activity; and arteriosclerosis associated with PDGF-AA activity.

Thus, in another aspect, the invention provides a pharmaceutical composition comprising a sulfated polysaccharide selected from the group consisting of sulfated alginate, sulfated hyaluronan, and both, and a pharmaceutically acceptable carrier, for treatment or inhibition of a disease or disorder caused by, or associated with, the activity of at least one bioactive polypeptide capable of binding a sulfate group of said sulfated polysaccharide, preferably in diseases or disorders caused by, or associated with, the activity of a bioactive polypeptide selected from the group consisting of platelet-derived growth factor BB (PDGF-BB), basic fibroblast growth factor (bFGF), vascular endothelial growth factor (VEGF), transforming growth factor β (TGFβ), acidic fibroblast growth factor (aFGF), interleukin-6 (IL-6), thrombopoietin (TPO), stromal cell derived factor-1 (SDF-1), hepatocyte growth factor (HGF), epidermal growth factor (EGF), insulin growth factor (IGF), platelet-derived growth factor AA (PDGF-AA), and a combination thereof.

In a preferred embodiment, the invention provides a pharmaceutical composition comprising a sulfated alginate and/or sulfated hyaluronan and a pharmaceutically acceptable carrier for the treatment of cancer.

In another aspect, the invention relates to a method for treatment of a patient suffering from a disease or disorder caused by, or associated with, the activity of at least one bioactive polypeptide capable of binding a sulfate group of a sulfated polysaccharide, which comprises administering to said patient an effective amount of a sulfated alginate, sulfated hyaluronan, or both.

In a preferred embodiment, the invention relates to a method for the treatment of a patient suffering from cancer.

The invention will now be described with reference to some non-limiting examples. The references provided throughout this document are provided for the convenience of the reader and all the information contained therein is incorporated herein by reference.

EXAMPLES

Example 1

Method of Alginate Sulfation and Product Analysis

To confer specificity on the alginate for its use as a delivery system, we developed the bioconjugate concept of alginate sulfate. The properties of alginate sulfate, such as biocompatibility, hydrophilicity, and the simple method of its formulation (physical cross-linking) as well as its low cost (of production and sulfation) are advantageous to its application for the controlled delivery of cytokines, growth factors and heparin-binding polypeptides, as well as a scaffold for tissue engineering.

Alginate sulfation was conducted by the sulfuric acid/carbodiimide method, essentially as described in U.S. Pat. No. 6,388,060, hereby incorporated by reference in its enterity as if fully described herein. In brief, the reaction is comprised of two steps: first, converting sodium alginate to alginic acid by batch ion exchange and then titration with tributylamine (TBA) yielding alginate-TBA. The second step consists of 0-sulfating the amine salt of alginate via carbodiimide chemistry (N,N'-dicyclocarbodiimide, DCC), with various molar ratios of the components: $DCC:H_2SO_4$:uronic acid. The degree of alginate sulfation was evaluated by Fourier-Transformed Infrared Spectroscopy (FTIR) and microanalysis.

Table 1 summarizes the different component molar ratio used for alginate sulfation and the resulting degree of alginate sulfation.

TABLE 1

| Sulfation reaction | |
|---|---|
| Uronic acid:$DCC:H_2SO_4$ (Molar Ratio) | Sulfation Degree (Uronic Acid:Sulfor) |
| 1:20:30 | 1:0.8 |
| 1:10:20 | 1:0.4 |
| 1:20:20 | 1:0.6 |

(i) Determination of Sulfation Degree

The sulfated alginate product was characterized by FTIR. Homogeneous pellets of the lyophilized product (0.0035 g) with potassium bromide (0.100 g; Fluka, Switzerland) were prepared by applying pressure (4.5 metric tons, CARVER, INC., WABASH, India).

Quantitative microanalysis by known methods estimated the ester sulfate content within the alginate sulfate product after its acid hydrolysis (Dodgson, 1960; Dodgson and Price, 1962). The liberated inorganic sulfur was estimated turbidimetrically as insoluble barium sulfate, at wavelength 360 nm, using a spectrophotometer and its amount was interpolated from a calibration curve for known concentration of $K_2SO_4$.

(ii) FTIR Analysis

Alginate sulfate was characterized by FTIR to reveal the changes in product versus the raw material, sodium alginate. The IR spectrum of alginate sulfate shows a new major peak at ~1250 $cm^{-1}$ and a minor peak at ~800 $cm^{-1}$ (FIG. 1). The peak at ~1250 $cm^{-1}$ is assigned to S=O symmetric stretching, while the one at ~800 $cm^{-1}$ for S—O—C stretching.

The degree of sulfation on sodium alginate was determined by analyzing the area under the peak (1325-1186 $cm^{-1}$).

Example 2

Biomolecular Interactions of Alginate Sulfate and Heparin-Binding Polypeptides by SPR Technology Real-time biomolecular interaction analysis was performed using the BIAcore 3000 instrument (Pharmacia Biosensor AB, Sweden), operated with BIA evaluation version 3.2 software. All experiments were preformed, at 25° C., using HBS (10 mM HEPES, 0.15M NaCl, 3 mM EDTA, 0.005% surfactant P20, pH 7.4) as a running and dilution buffer.

(i) Immobilization of the ligands to sensor chip: The different polysaccharide samples were immobilized onto the sensor chip via biotin-avidin chemistry. Biotinylated sample of heparin-albumin was purchased from Sigma-Aldrich Chemicals (St Lewis, Mich.) and biotinylated samples of alginate and alginate sulfate were prepared using the method described in Polyak et al (2004). The biotinylated samples of the polysaccharides were immobilized onto streptavidin sensor chip (SA, Pharmacia Biosensor AB) as follows: the sensor chip was pulsed three times with 1 min-injections of 50 mM NaOH, 1M NaCl at flow rate of 10 μl/min, to remove non-covalently bound streptavidin from the sensor surface. Flow-cell 1 (FC-1) remained with no immobilized ligand for reduction of non-specific interactions of the analyte with the sensor chip SA. The positive control, biotinylated heparin-albumin (10 μg/ml in HBS buffer) was injected to FC-2 for 1 min, at a flow rate of 10 μl/min, to achieve covalent immobilization of 300 RU on the biosensor surface. In FC-3, a similar amount of biotinylated alginate sulfate (10 μg/ml in HBS buffer) was immobilized to the surface. The injection was stopped after 5 μl after achieving RU similar to the positive control. In FC-4, immobilization of the negative control, biotinylated alginate, was done the same way.

(ii) Binding of heparin-binding polypeptides: Binding assays were performed over a range of polypeptide concentrations (Table 2) (in increments of 100 nM). The protein was diluted with HBS buffer immediately prior to injection (flow rate of 20 μl/min, 4 min, dissociation time was 3 min). The sensor chip was regenerated by injections of NaCl (1M, 1 min, 20 μl/min).

(iii) Data analysis: The real-time reference curve obtained form a nonligand coated flowcell exposed to HBS buffer (FC-1) was subtracted from binding curves obtained from the flowcells with immobilized ligands. Association and dissociation rate constants were calculated by nonlinear curve fitting of the primary sensorgram data using the (Langmuir) binding model available in the BIAEVALUATION 3.1 software. The affinity constants (K) were calculated from the association and dissociation rate constants using the software.

TABLE 2

Peptide type and concentration range in SPR studies

| # | Peptide | Peptide (abbreviated) | Concentration Range (nM) |
|---|---|---|---|
| 1 | Platelet-derived growth factor BB | PDGF-BB | 50–300 |
| 2 | Basic fibroblast growth factor | bFGF | 200–600 |
| 3 | Vascular endothelial growth factor | VEGF | 500–5000 |
| 4 | Transforming growth factor β1 | TGFβ1 | 80–300 |
| 5 | Acidic fibroblast growth factor | aFGF | 10–50 |
| 6 | Interleukin 6 | IL-6 | 100–1400 |
| 7 | Thrombopoietin | TPO | 200–1000 |
| 8 | Stromal Cell Derived Factor-1 | SDF-1 | 100–600 |
| 9 | Hepatocyte growth factor | HGF | 50–250 |
| 10 | Epidermal growth factor | EGF | 500–5000 |
| 11 | Insulin growth factor | IGF | 5000–25000 |
| 12 | Platelet-derived growth factor AA | PDGF-AA | 450–700 |
| 13 | FLT | FLT-3 | No specific binding to alginate sulfate |
| 14 | Stem cell factor | SCF | No specific binding to alginate sulfate |
| 15 | Oncostatin | OCM | No specific binding to alginate sulfate |

Of the molecules studied in Table 2, peptides 1-12, which are known to be heparin-binding peptides, according to published literature, showed specific binding to alginate sulfate, while no such interactions were observed with non modified alginate (FIG. 2A-13A). The SPR sensorgrams (FIG. 2B-12B) of peptide binding to alginate sulfate, over a range of peptide concentrations (Table 2) showed that the interactions fit the Langmuir 1:1 binding model, with equilibrium binding constants detailed in Table 3.

The specificity of interactions can be also seen in the finding that peptides, which do not belong to the heparin-binding peptides class (peptides 13-15, in Table 2) did not interact with alginate sulfate or with heparin.

Sulfation of unsulfated uronic acid-containing alginates converted these polysaccharides into a biologically active species. The monomer β-D-Mannuronic acid in alginate differs from the uronic acid in heparan sulfate (HS) at positions C2 or C3, where in the later; sulfate group replaces the hydroxyl group. This structure similarity has lead us to the hypothesis that alginate sulfate may substitute HS in terms of its interactions with heparin-binding growth factors such as bFGF. The heparin-binding peptides interact with heparin or heparan sulfate via regions containing IdoA (-2-$SO_3$) and GlcN$SO_3$ residues (Casu and Lindahl, 2001) wherein the sulfate groups play central role in binding (Wu et al, 2003).

TABLE 3

Binding to Alginate Sulfate compared to Heparin (this work and literature)

| Peptide | Ligand | $K_A$ (M$^{-1}$) | $K_D$ (M) | $\chi^2$ | $K_D$ (M) (Literature) |
|---|---|---|---|---|---|
| 1 PDGF-BB | Heparin | $1.33 * 10^6$ | $7.51 * 10^{-7}$ | 10.1 | — |
| | Alginate-sulfate | $35.3 * 10^6$ | $0.28 * 10^{-7}$ | 9.09 | |
| 2 bFGF | Heparin | $1.7 * 10^7$ | $6.0 * 10^{-8}$ | 19.9 | $7.13 * 10^{-8}$ (Xiao-feng, Ya-xiang et al. 2003) |
| | Alginate-sulfate | $9\text{-}20 * 10^7$ | $0.5\text{-}1.11 * 10^{-8}$ | 17.1 | |
| 3 VEGF | Heparin | $9.68 * 10^7$ | $1.03 * 10^{-8}$ | 15.8 | $\sim 2 * 10^{-8}$ (Cochran et al, 2003) |
| | Alginate-sulfate | $2.2\text{-}3.2 * 10^7$ | $3.2\text{-}4.5 * 10^{-8}$ | 11.4 | |
| 4 TGFβ1 | Heparin | $2.38 * 10^7$ | $4.2 * 10^{-8}$ | 13.9 | — |
| | Alginate-sulfate | $2.31 * 10^{12}$ | $7.32 * 10^{-13}$ | 8.03 | |
| 5 aFGF | Heparin | $7.9 * 10^7$ | $1.26 * 10^{-8}$ | 9.66 | $18 \pm 3.0 * 10^{-8}$ (Kamei, Wu et al. 2001) $16.0 * 10^{-8}$ (Zhang, Fath et al. 2002) |
| | Alginate-sulfate | $2.8 * 10^7$ | $3.59 * 10^{-8}$ | 5.84 | |
| 6 IL-6 | Heparin | $1.12 * 10^7$ | $8.91 * 10^{-8}$ | 6.86 | — |
| | Alginate-sulfate | $1.38 * 10^7$ | $7.27 * 10^{-8}$ | 5.32 | |
| 7 TPO | Heparin | — | — | — | — |
| | Alginate-sulfate | $1.81 * 10^6$ | $5.53 * 10^{-7}$ | 0.679 | |
| 8 SDF-1 | Heparin | $1.65 * 10^7$ | $6.06 * 10^{-8}$ | 11.9 | $3.84 * 10^{-8}$ (Amara, Lorthioir et al. 1999) |
| | Alginate-sulfate | $20.6 * 10^7$ | $0.485 * 10^{-8}$ | 12.7 | |
| 9 HGF | Heparin | $1.19 * 10^8$ | $8.42 * 10^{-9}$ | 4.64 | $1.00 * 10^{-9}$ (Rahmoune, Rudland et al. 1998) |
| | Alginate-sulfate | $0.536 * 10^8$ | $18.7 * 10^{-9}$ | 1.88 | |
| 10 EGF | Heparin | $8.38 * 10^6$ | $1.19 * 10^{-7}$ | 0.794 | — |
| | Alginate-sulfate | $9.93 * 10^6$ | $1.01 * 10^{-7}$ | 0.354 | |
| 11 IGF | Alginate-sulfate | $1.01 * 10^8$ | $1 * 10^{-8}$ | 0.86 | |
| 12 PDGF-AA | Alginate-sulfate | $2.35 * 10^{11}$ | $4.26 * 10^{-12}$ | 25 | |

Example 3

Sustained Release from Alginate/Alginate Sulfate Capsules

The example shown herein examines the capability of alginate sulfate to sustain the release of the angiogenic heparin-binding peptide, bFGF, from microspheres compared to microspheres composed of only unmodified alginate.

(i) Microsphere preparation and bFGF encapsulation: Sodium alginate (high G content, FMC Biopolymers) solution 1% (w/v DDW) was mixed in different volume proportions with alginate sulfate solution 1% (w/v DDW). bFGF (0, 0.2, 0.5, 1, 2 µg/ml) was added to alginate/alginate sulfate mixture, and incubated for 1 h, 37° C. The mixture was collected into a syringe (18G) and was dropped into stirred CaCl$_2$ solution (10-12 ml, 0.15M). The capsules were allowed to stir at room temperature for 0.5 h until gelation is complete and centrifuged (1500 RPM, 25° C., 10 min). The supernatant was removed and a sample (1 ml) from the capsules containing bFGF was suspended in 1 ml culture medium (CM) DMEM (1% Pen-Strep Biological Industries, Israel). Release studies were conducted by incubating the capsules on a rotating incubator at 37° C. The CM was semi-replaced daily (0.5 ml) and the amount bFGF in releasing media was determined by an ELISA. All the experiments were preformed in a sterile environment.

Analysis of Released bFGF by ELISA: Samples from releasing medium were diluted 1:10 with PBS buffer (pH=7.4, NaCl 137 mM, Na$_2$HPO$_4$ 8 mM, KCl 2.7 mM, KH$_2$PO$_4$ 1.5 mM, Sigma) and placed (100 µl/well) in 96 wells polyvinylchloride (PVC) plate overnight, 4° C. After washing twice with 300 µl/well PBST (PBS buffer, pH 7.4, 0.05% Twine 20), residual protein binding sites in the wells were saturated by incubating with 250 µl/well of blocking solution (PBS, 2% BSA) either at 4° C. overnight or for 2 h at 37° C. (shaking). After three washes with PBST (300 µl/well), 100 µl of the growth factor-specific detection antibody (2 µg/ml Goat polyclonal anti bFGF in PBS, 1% BSA, R&D systems Inc,), was allowed to incubate in the wells for 1 h, 37° C., (shaking). After another round of washing (PBST 300 µl/well ×8) 100 µl of streptavidin, HPR conjugated (1 µg/ml PBS 1% BSA, Chemicon International) was added and incubated for 1 h at room temperature in dark. Wells were then washed and bound HPR was detected by addition of 100 µl of TMB (Chemicon International) as a peroxidase substrate. The reaction was stopped after 5 min by an addition of 50 μl of 0.5M $H_2SO_4$. The absorbance of the yellow reaction product was then measured at 450 nM on a plate reader (Bio-Tek instruments, EL808). Standards bFGF (6.25, 3.125, 1.56, 0.8, 0 ng/ml) had been used for calibration.

Figure 14:
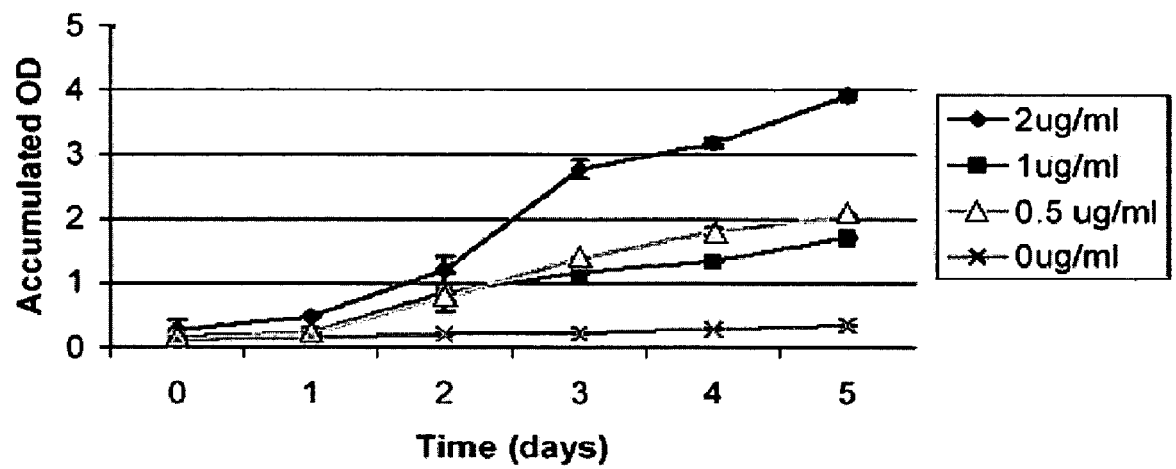
FIG. 14 shows bFGF release profile from alginate capsules fabricated from alginate sulfate. bFGF solutions with a range of concentrations were incubated with alginate/alginate sulfate solution for binding and then the capsules were produced. Released bFGF was analyzed by ELISA.
Figure 15:
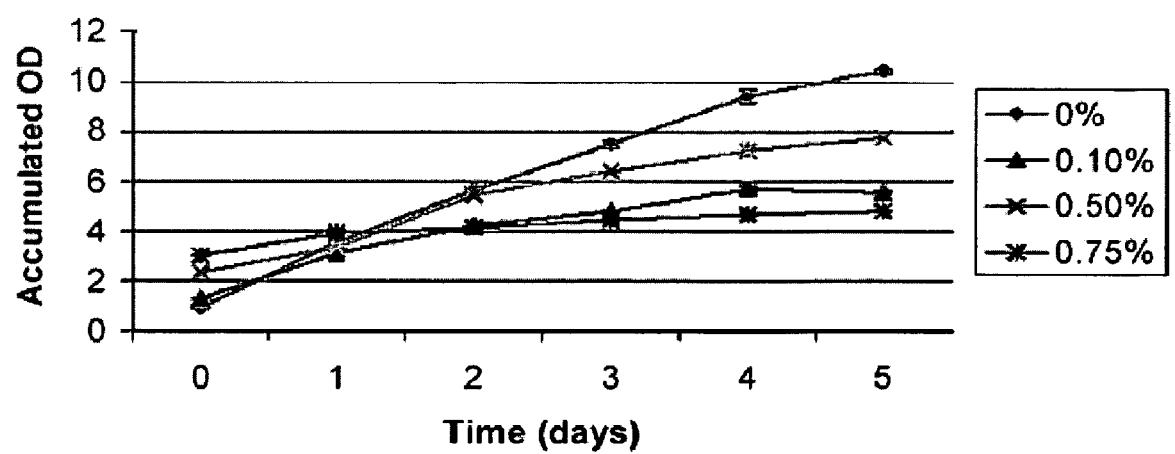
FIG. 15 shows the release profile of bFGF from capsules containing different amounts of alginate sulfate (0, 0.1, 0.5, 0.75, 1% w/v) and the remaining to total of 1% (w/t) was non-modified alginate. bFGF (2 µg/ml) was incubated for binding prior to capsule formation. The released bFGF was analyzed by the direct ELISA method.

The study rationale was to verify whether capsules containing alginate sulfate can sustain bFGF release and presentation. Two initial studies were performed to optimize the amounts of alginate sulfate and bFGF within the capsules. In the first, the amount of alginate sulfate in alginate/alginate sulfate solution was maintained constant (0.9%/0.1%, w/v, respectively) while bFGF concentrations were varied (0, 0.2, 0.5, 1, 2 μg/ml of alginate/alginate sulfate solution). The polymer mixture solution and bFGF solution were incubated 37° C., 1 h, for binding before capsulation. During release study, the capsules were incubated in 1 ml culture medium for 5 days at 37° C. and the medium was partially (0.5 ml) replaced daily with a fresh one. The collected medium with the liberated bFGF was analyzed by ELISA. The results in FIG. 14 are presented as accumulated OD vs. time. As seen, the release rate is fairly constant and proportional to bFGF concentrations initially encapsulated in the capsules. The second study aimed at optimizing the amount alginate sulfate added (0, 0.1, 0.5, 0.75, 1% w/v) into the mixture alginate/ alginate sulfate with excess of bFGF (2 μg/ml). After binding and capsule formation, release studies were preformed. We found that a 0/1 (% wt ratio) mixture of alginate/alginate sulfate did not form stable capsules in the presence of $CaCl_2$, while the other mixtures did form. The samples were analyzed by ELISA and the results are presented as accumulated OD (FIG. 15). It is shown that alginate sulfate in the capsules sustained bFGF release to the medium. As the amount of alginate sulfate in the capsules increased, less bFGF was released to the external medium.

Figure 16:
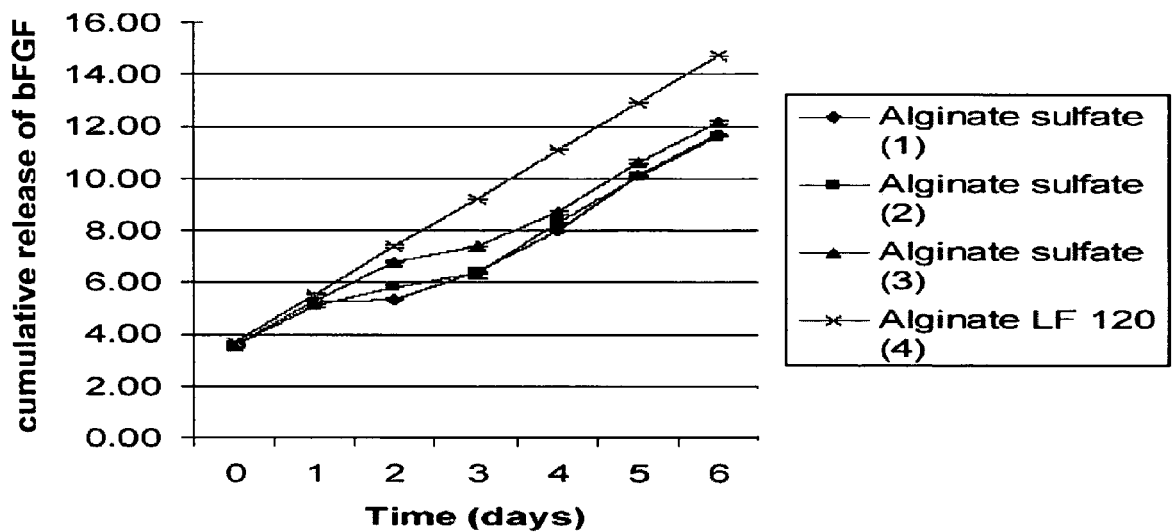
FIG. 16 shows bFGF release from 3 different batches of alginate capsules containing 0.1% alginate sulfate, compared to control capsules. BFGF-containing capsules were placed with medium and incubated at 37° C. for 6 days, and the released bFGF was analyzed by ELISA. The results were interpolated from the calibration curve plotted for known concentrations of bFGF.
Figure 17:
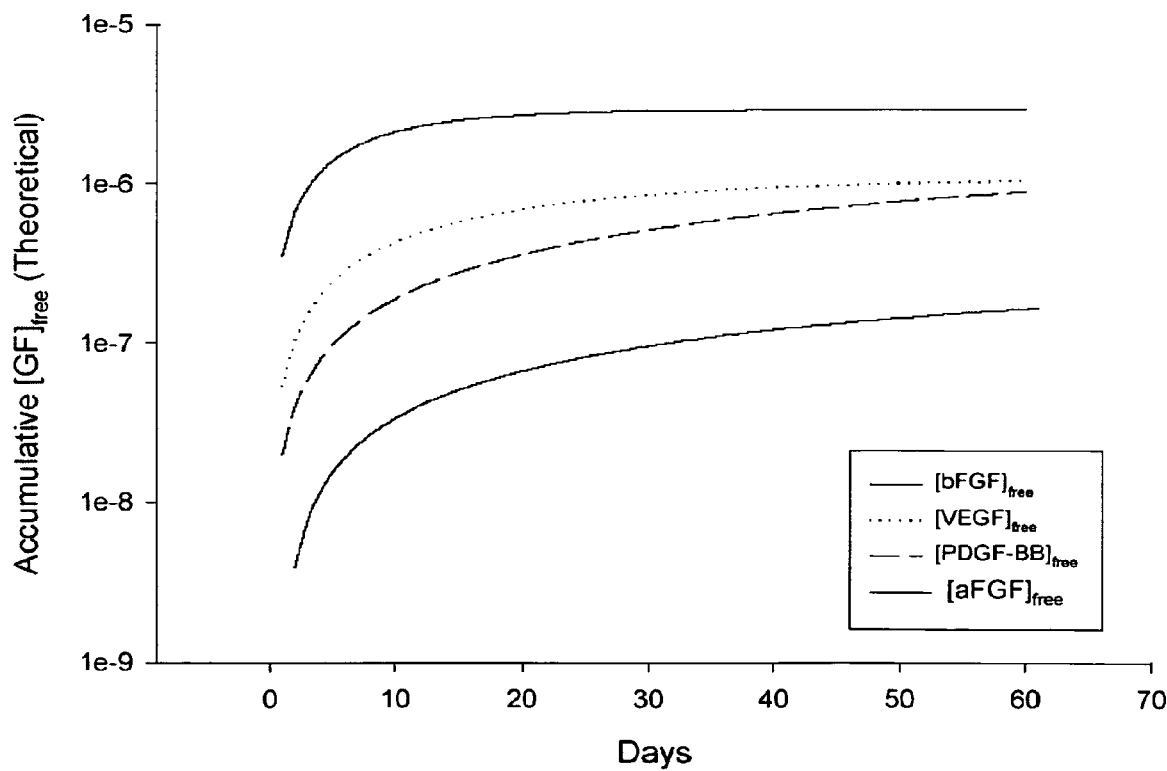
FIG. 17 shows theoretical accumulative (molar concentration) releasing profile of the growth factors: bFGF, VEGF, aFGF, PDGF-BB (for 1 µg loading).

Based on these studies, an optimal formulation was developed. It consisted of a mixture of alginate/alginate sulfate (9:1 wt ratio) at a final polymer concentration of 1% (w/v), and incorporated 0.2 μg/ml bFGF. bFGF release from three batches of such capsules was evaluated over a 6-day period. Control capsules were made of only sodium alginate (LF-120, Nova Matrix, high G) 1% (w/v) and adsorbed bFGF (0.2 μg/ml). The formulations were incubated as described above and the released bFGF was analyzed by ELISA. bFGF content was interpolated from a calibration curve of known bFGF concentrations. The results are presented as accumulated bFGF concentrations in medium (FIG. 16).

The release rate of bFGF from the alginate/alginate sulfate composite capsules was fairly constant, after an initial burst of 30%, showing a nearly linear release pattern. Faster release rates were seen from the capsules with no alginate sulfate. By day 6, approx 90% of the encapsulated growth factor in control capsules was released to the external medium, while in the composite alginate sulfate containing capsules approximately 70% release was seen.

We tested the capability of the alginate sulfate based delivery system to co-encapsulate 4 important angiogenic factors and release them at a sustained manner, depending on their $K_A$ equilibrium binding to alginate sulfate and the initial concentration of encapsulated peptide. The four factors included VEGF, bFGF, aFGF and PDGF-BB, which are responsible for inducing blood vessel formation and maturation. The concentration of free peptide (correlates to released peptide) was calculated according to the following equation (derived from the equilibrium binding equation assuming that alginate concentration is well above that of the peptide so that we consider total alginate concentration is equal to that of free one)

$$[GF]_{free} = \frac{[GF]_{Total}}{(1 + K_A \cdot [AlgSO_3]_{Total})}$$

The results shown herein reveal that VEGF is released at a faster rate compared with PDGF-BB. Such pattern will be suitable for blood vessel growth and maturation. At earlier stages of blood formation, the presence of VEGF is necessary for forming the vessel and later PDGF-BB stabilizes the vessels by recruiting mural cells.

Example 4

In-Vivo Angiogenesis and Scaffold Vascularization

In this example, we show that the novel alginate/alginate sulfate system is capable of sustaining the release and presentation of the heparin-binding peptides also in vivo. For a proof of concept, we tested this system for the sustained delivery of a single angiogenic factor (bFGF) and for the co-delivery of multiple angiogenic factors (VEGF, PDGF-BB and TGF-β). We compared the kinetics and extent of in vivo angiogenesis compared with peptides delivered from non modified alginate systems (thus providing an instant release).

To enable a simple determination of blood vessels in the in vivo set up, the delivery systems were fabricated as macroporous (~100 μm pore size) scaffolds, which enable blood vessel penetration without obstructions. Another advantage of the scaffold system is its potential application for tissue engineering and regeneration.

Preparation of Porous Scaffolds and Characterization: Alginate/alginate sulfate scaffolds, diameter 11 mm, thickness 3 mm, were prepared from a mixture of alginate with high guluronic acid (G) content (>65% G; FMC Biopolymers) and alginate sulfate (9:1 wt ratio) by a freeze-dry technique as previously described (Shapiro and Cohen, 1997). In brief: alginate and alginate sulfate were dissolved separately in DDW to obtain 1.25% (w/v) solutions. Sterilization of sodium alginate was achieved by filtration through 0.2 μm filter under $N_2$ pressure. Cross-linking was achieved by adding D-gluconic acid hemi-calcium ion solution (1% w/v, Sigma, Israel) to the mixture while being homogenized (26,000 rpm, DIAX 900 Heidolph, Germany). The mixtures were pulled into 48 wells plates (250 μl/well) chilled to 2°-8° C. over night, frozen at −20° C. for 24 h and then lyophilized. Scaffolds sterilization was achieved by ethylene oxide or with ultra-violet (UV) light (1 h, 25° C.).

Figure 18:
FIGS. 18A-18B show the SEM morphology of alginate/alginate sulfate scaffolds (18A) versus plain alginate scaffolds and (18B), showing that there is no difference in morphology.
Figure 18:
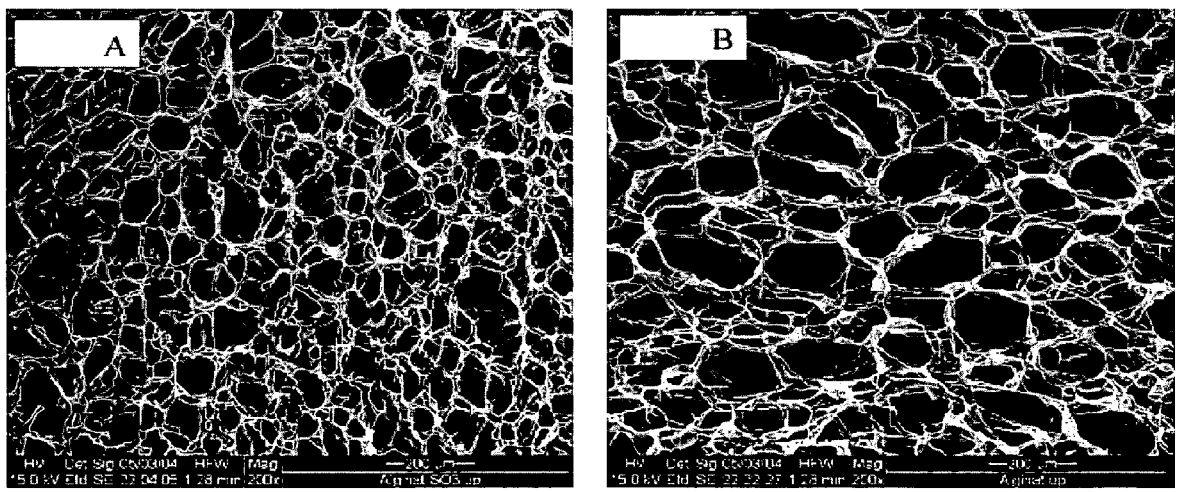
Figure 19A:
FIGS. 19A-19C show the appearance of implanted scaffolds 14 days post-implantation. (19A) In the study group with alginate/alginate sulfate and 10 µg bFGF/scaffold, a large capsule full with blood liquid is observed, (19B) in control I group, with alginate and 10 µg bFGF/scaffold, no capsule observed, the scaffolds are partially eroded (arrow); and (19C) in control II with alginate/alginate sulfate without bFGF, the arrow point at scaffold with no capsule. Macroscopic view of hematoxylin and eosin (H&E) stained cross-sections of the scaffold implants and the surrounding tissue, 2 weeks after implantation, are shown on the right: (19A1) Study group, (19B1) Control I and (19C1) Control II (bar indicates 2 mm).
Figure 19A:
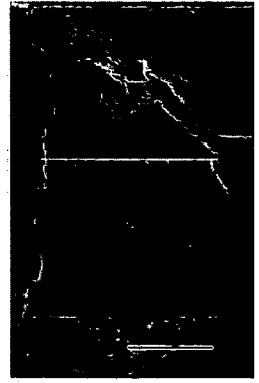
Figure 19B:
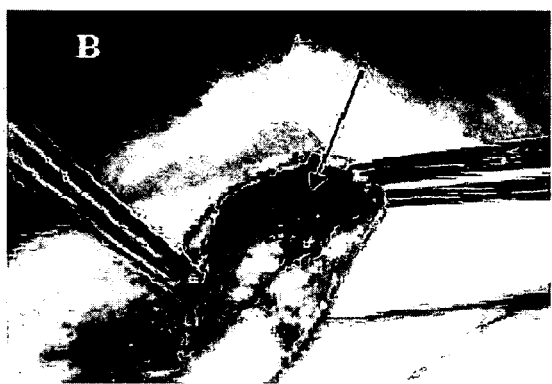
Figure 19B:
Figure 19C:
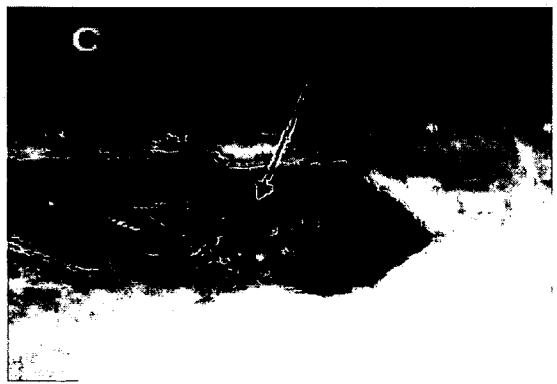
Figure 19C:
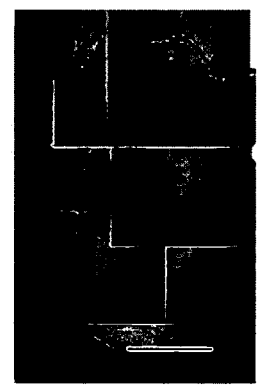

FIG. 18 shows a picture of the alginate/alginate sulfate scaffold and its SEM (scanning electro microscope) morphology. When compared to scaffold made of non modified alginate, there is no measurable difference in morphology.

(i) Feasibility Studies with Basic FGF Incorporated into Alginate/alginate Sulfate Composite Scaffolds (Single Peptide System).

Composite scaffolds of alginate/alginate sulfate (9:1, wt ratio, total of 1% w/t solution) were implanted subcutaneously in the dorsal area in Sprague Dawley rats, two scaffolds in each rat. Prior to implantation, the scaffolds were incubated for 1 h, at 37° C., in 80 μl culture medium with or without bFGF. Additional control group was implanted with alginate scaffolds incorporating bFGF by adsorption (Table 4).

TABLE 4

Experimental and control groups in the study

| Group | Scaffold type | bFGF (µg/scaffold) | n |
|---|---|---|---|
| Study | alginate/alginate sulfate | 10 | 4 |
| Control I | alginate | 10 | 4 |
| Control II | alginate/alginate sulfate | 0 | 2 |

At day 14 post-implantation, the rats were sacrificed and the implanted scaffolds and surrounding tissues were removed together, fixed in formalin, paraffin embedded, sectioned and stained with hematoxylin and eosin (H&E). In the study group implanted with bFGF-composite scaffolds, the implants were surrounded by a large capsule. All capsules were thick and full with serotic blood liquid, with no sign of infection (FIG. 19). In both the control groups I and II, no capsules were found. In control group I, implanted with alginate scaffolds with adsorbed bFGF disassembled scaffolds were found attached to the subcutaneous tissue with no sign of infection. In control group II, implanted with alginate/alginate sulfate with no bFGF, the scaffolds were found entirely whole with no sign of infection as well.

Figure 20A:
FIGS. 20A-20C show high magnification pictures of H&E stained cross-sections in the scaffold implants, 2 weeks post implantation, (20A) the study group alginate/alginate sulfate/bFGF; (20B) Control I alginate bFGF; and (20C) Control II alginate/alginate sulfate (bar indicates 100 µm).
Figure 20B:
Figure 20C:
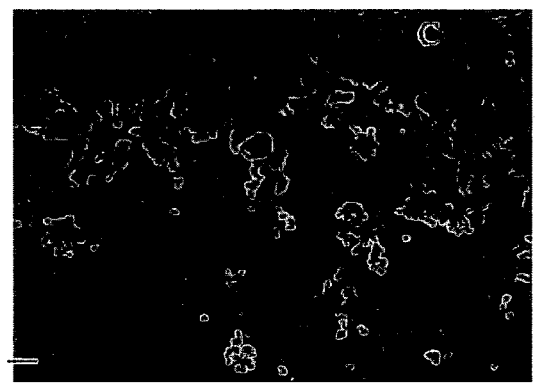

Lower magnification pictures of cross sections in the implant, stained with H&E, are shown on the right side of FIG. 19. Cross-sections in the bFGF incorporating alginate/alginate sulfate composite scaffolds (FIG. 19A) show a thick capsule surrounding the scaffold and significant tissue penetration into scaffold. Lesser extent of tissue penetration was found in alginate scaffold adsorbed with 10 µg of bFGF (FIG. 19B). In alginate/alginate sulfate scaffolds, with no bFGF supplementation (FIG. 19C), tissue ingrowth was minimal. Higher magnification pictures (FIG. 20) show that the penetrating tissue is confined within the scaffold pore walls that were not degraded at this time point. In the control groups (I and II), most of the scaffold pores had no tissue.

Figure 21:
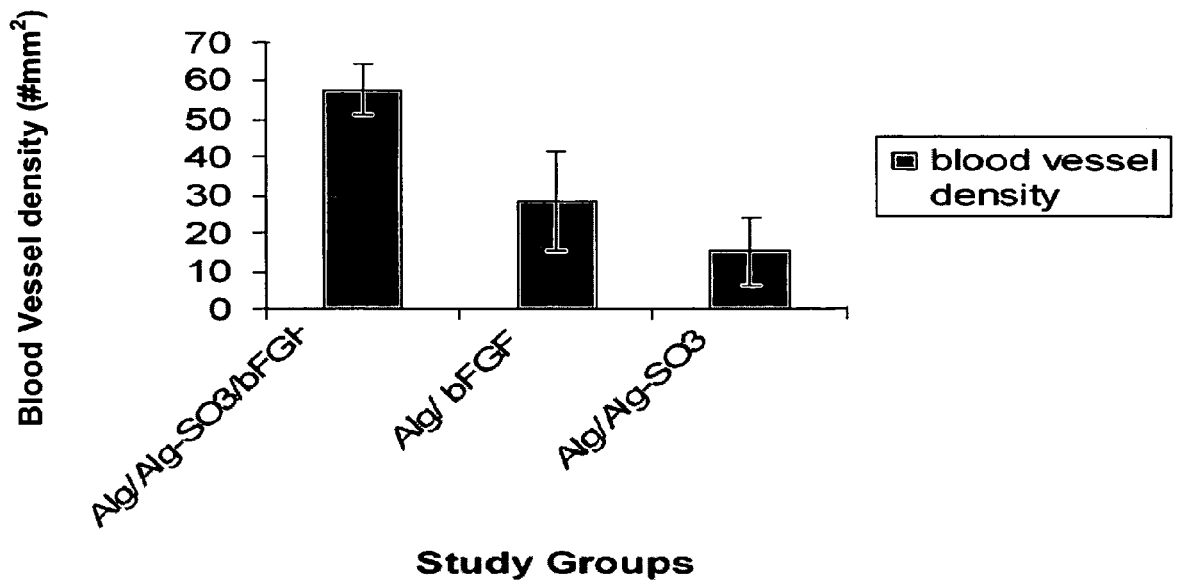
FIG. 21 shows blood vessel density (number per area $mm^2$) in the implanted scaffolds with alginate/alginate sulfate/bFGF, alginate bFGF, and alginate/alginate sulfate, 14 days post-implantation. P<0.05 (*)

Blood vessel density (number per $mm^2$) (FIG. 21) and the percentage area occupied by them (FIG. 22), were determined in 10 different fields/slide, randomly selected from H&E cross sections slides, using Scion image NIH software. The focus of analysis was on the capsule membrane surrounding the implants since our intention was to examine release outside the scaffold. Collectively, theses results show that controlled release of bFGF from alginate/alginate sulfate scaffolds enhanced scaffold vascularization. On day 14 post-implantation, 57.6±6.8 blood vessels/$mm^2$ were counted in bFGF releasing scaffolds made of alginate/alginate sulfate, while only 28.2±13.2 and 15.1±8.8/$mm^2$ were found in the FGF-adsorbed alginate scaffolds and alginate sulfate (with no bFGF), respectively. The difference between the study/control I and study/control II group is significant (analysis of variance, ANOVA single factor, $P<0.05$) while the difference between the two control groups is not significant ($P>0.05$).

Figure 22:
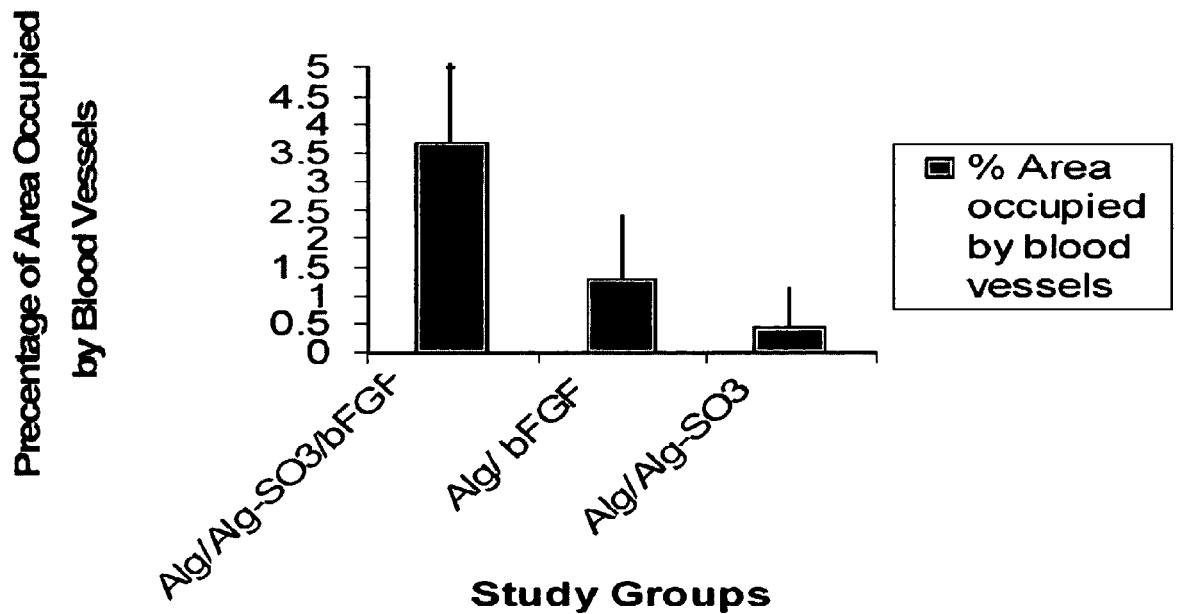
FIG. 22 shows the percentage of area occupied by blood vessels in the implanted scaffolds with alginate/alginate sulfate/bFGF, alginate bFGF, and alginate/alginate, 14 days post-implantation. P<0.05 (*).

The percentage of area occupied by blood vessels was also analyzed on sections of the implanted scaffolds. This analysis takes into account the size of the blood vessels. FIG. 22 shows that the area occupied by blood vessels is 2.9 times higher in the bFGF releasing alginate/alginate sulfate scaffolds than in groups implanted with bFGF adsorbed alginate scaffolds and 8.3 times higher than similar scaffolds without bFGF supplementation. These results indicate that controlled bFGF delivery enhances scaffold vascularization.

Figure 23:
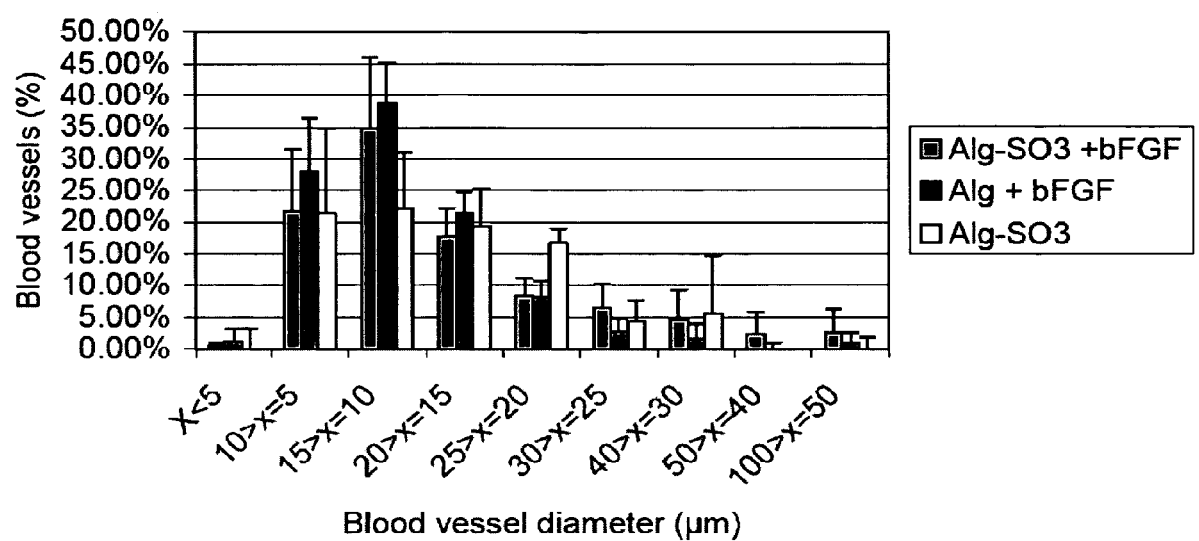
FIG. 23 shows the distribution of blood vessel diameters within the implanted scaffolds with alginate/alginate sulfate/bFGF, alginate bFGF, and alginate/alginate, 14 days post-implantation. The Y-axis is the % number of blood vessels in each category in every group.

The distribution of blood vessel size was also analyzed by measuring their median diameter, using Scion image NIH software. Due to variations in vessel shape, the smaller diameter assuming elliptic shape for the vessels was taken as a representative diameter. The blood vessels were divided randomly according to their size, into 9 groups: $x<5$, $10>x\geq5$, $15>x\geq10$, $10>x\geq15$, $25>x\geq20$, $30>x\geq25$, $40>x\geq30$, $50>x\geq40$, $100>x\geq50$ µm. FIG. 23 shows the diameter distribution of the newly formed blood vessels in the implanted scaffolds. Most of the blood vessel in all groups had diameter size of 5 to 20 µm. In the bFGF-releasing alginate/alginate sulfate scaffolds, blood vessels with larger diameters (>50 µm) were also found.

Figure 24A:
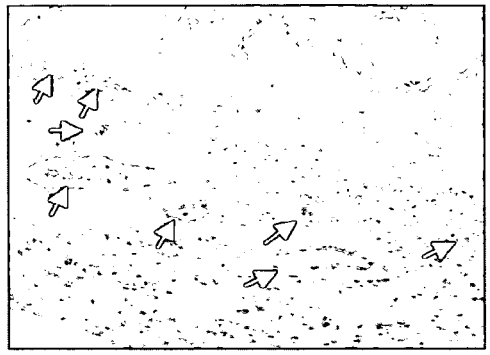
FIGS. 24A-24F show H&E histology of the capsule surrounding the implanted scaffolds. The bFGF-releasing alginate/alginate sulfate scaffolds have high cellular content and the blood vessels are large (24A, 24B). In contrast, the control groups have lower cellular content as well as blood vessels. (24C, 24D) Control I and (24E, 24F) Control II (bar indicates 100 µm).
Figure 24B:
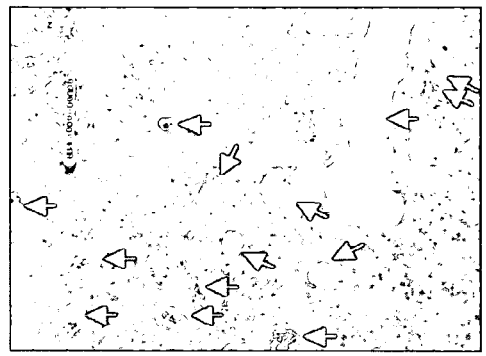
Figure 24C:
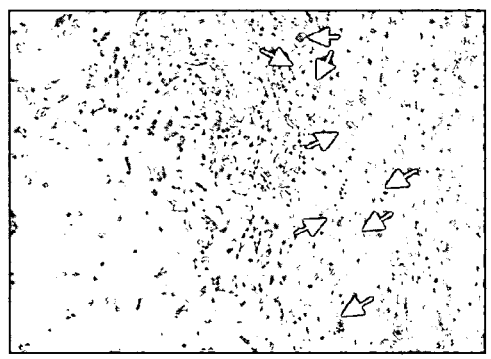
Figure 24D:
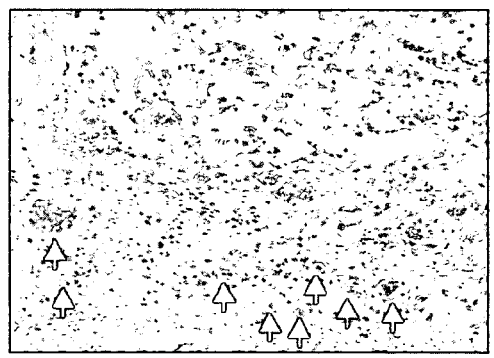
Figure 24E:
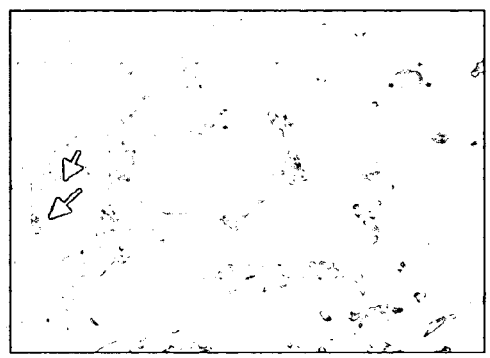
Figure 24F:
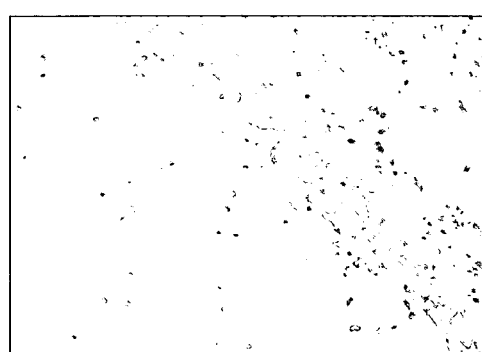

Next, the fibrotic capsule surrounding the scaffold was scanned, to evaluate differences between the different groups. The pictures presented in FIG. 24 reveled that the bFGF releasing alginate/alginate sulfate scaffolds were surrounded by a thick cellular capsule that was enriched with large blood vessels (FIG. 24A, B). In the group implanted with bFGF adsorbed to alginate scaffold, the surrounding capsule was thinner (FIGS. 24C, D) and in those implanted with alginate/alginate sulfate scaffolds, but no bFGF, the capsule was minimal (FIGS. 24E, F). As seen, there is an affect of bFGF on angiogenesis; however, this affect is magnified by the controlled delivery of the growth factor over time.

We further performed immunohistochemistry, examining the maturity state of the blood vessel (staining for isolectin and smooth muscle actin). In addition, we stained for the marker ED-1 which is expressed on macrophages (FIG. 25).

Figure 25:
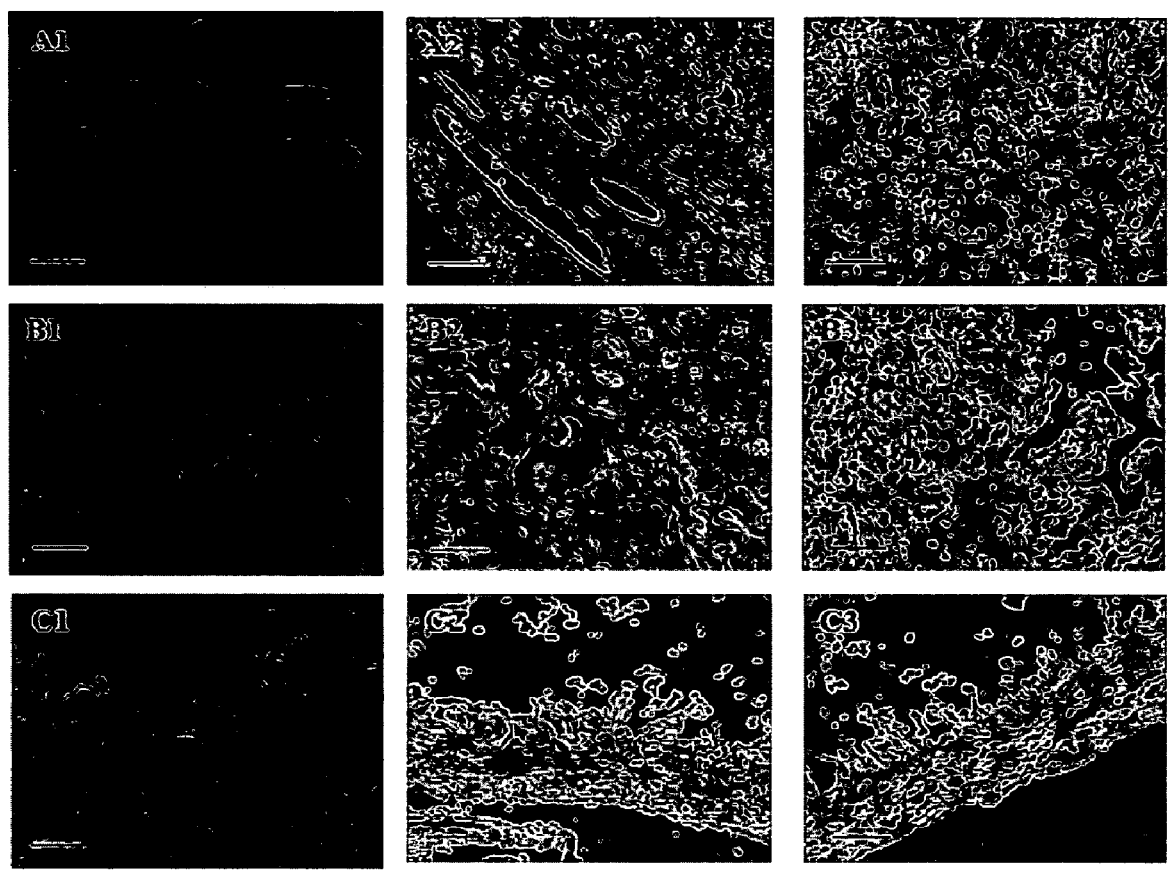

FIG. 25 shows high magnification pictures of immunostained cross-sections in the implant, 14 days after implantation. The presence of smooth muscles cell indicates the maturation of the formed blood vessels [Blood vessels are composed of three main layers: Tunica Intima; an endothelium that lines the lumen of all vessels, Tunica media; smooth muscles cells and elastic fibers and tunica adventitia; collagen fibers]. FIGS. 25A-C1 show positive staining for smooth muscle actin ($\alpha$SMA), indicating the presence of smooth muscle cells that are surrounding the newly formed blood vessels and their maturation. Most of the blood vessels in the capsule of the Alginate/alginate sulfate/bFGF group (A1) are surrounded by smooth muscle cells, while those in the control groups are less stained, showing much less angiogenesis and matured blood vessels. Endothelial cells are stained with anti lectin ($\alpha$ lectin) (FIGS. 25A-C2). Staining with $\alpha$-lectin marks the formed blood vessels surrounded the implant. ED1 staining of the macrophages suggests host immune reaction to the implant (FIGS. 25A-C3), probably as part of a wound healing process. The staining is minimal for the scaffold with no bFGF, while it is intense in the group wherein bFGF is adsorbed to the alginate scaffold and thus is released rapidly. Thus, the presence of large amount of bFGF at implant site, at a given time point, causes increased inflammation, while sustained delivery of bFGF over time diminishes this effect.

Example 5

Multiple Angiogenic Factor System Based on Alginate/Alginate Sulfate Composite Scaffolds Composite scaffolds of alginate/alginate sulfate (9:1, wt ratio, total of 1% w/t solution) were implanted subcutaneously in the dorsal area in SD rats, two scaffolds in each rat. Prior to implantation, the scaffolds were incubated for 1 h, at 37° C., in 80 µl culture medium with a single factor bFGF or a mixture of angiogenic growth factors (according to Table 5). Two control groups were implanted with alginate scaffolds incorporating bFGF or the mixture of the factors by adsorption (Table 5). Additional control group consisted of implanting the alginate/alginate sulfate scaffold, with no growth factor.

TABLE 5

Experimental and control groups in the study

| Group | Scaffold type | Angiogenic Factor (total of 100 ng/scaffold) | n |
|---|---|---|---|
| Study I | alginate/alginate sulfate | bFGF | 6 |
| Study II | alginate/alginate sulfate | VEGF, PDGF-BB, TGF-β 0.6:1:1 molar ratio | 6 |
| Control I | alginate | bFGF | 6 |
| Control II | alginate | VEGF, PDGF-BB, TGF-β 0.6:1:1 molar ratio | 6 |
| Control III | alginate/alginate sulfate | 0 | 6 |

Figure 26:
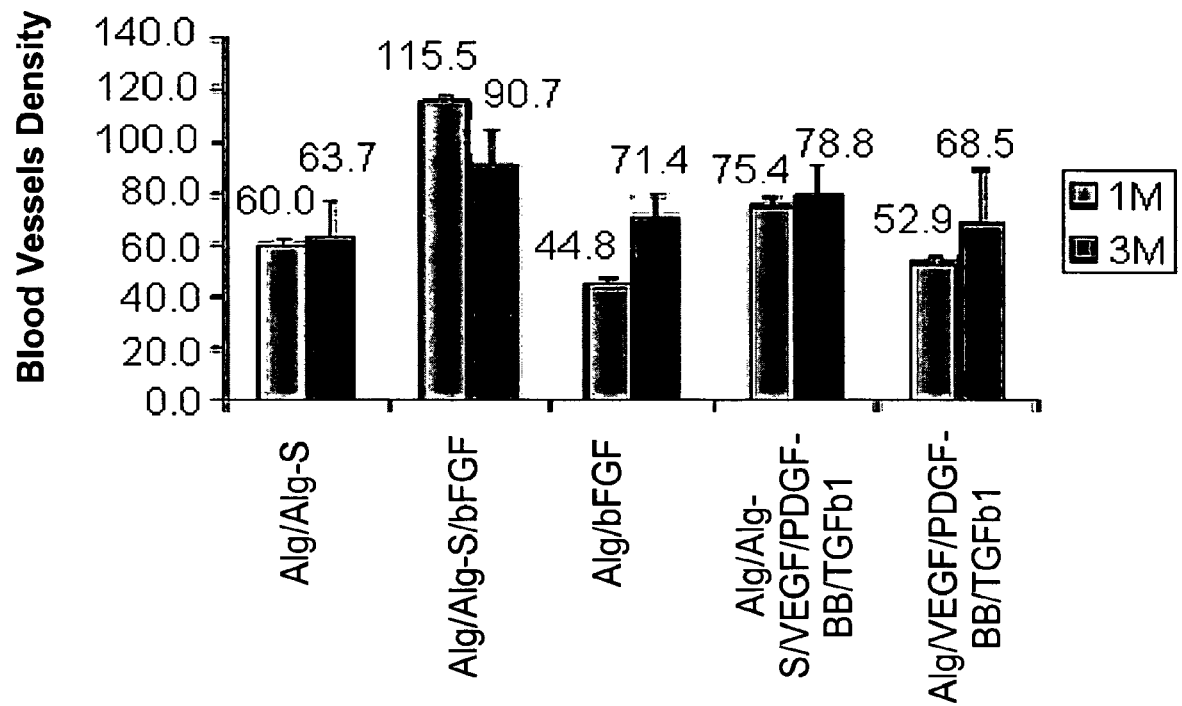
FIG. 26 shows blood vessel density (number per area $mm^2$) in the implanted scaffolds with alginate/alginate sulfate, alginate/alginate sulfate/bFGF, alginate/bFGF, alginate/alginate sulfate/VEGF/PDGF-BB/TGFβ1, or alginate/VEGF/PDGF-BB/TGFβ1, 1 and 3 months post-implantation. P<0.05.
Figure 27:
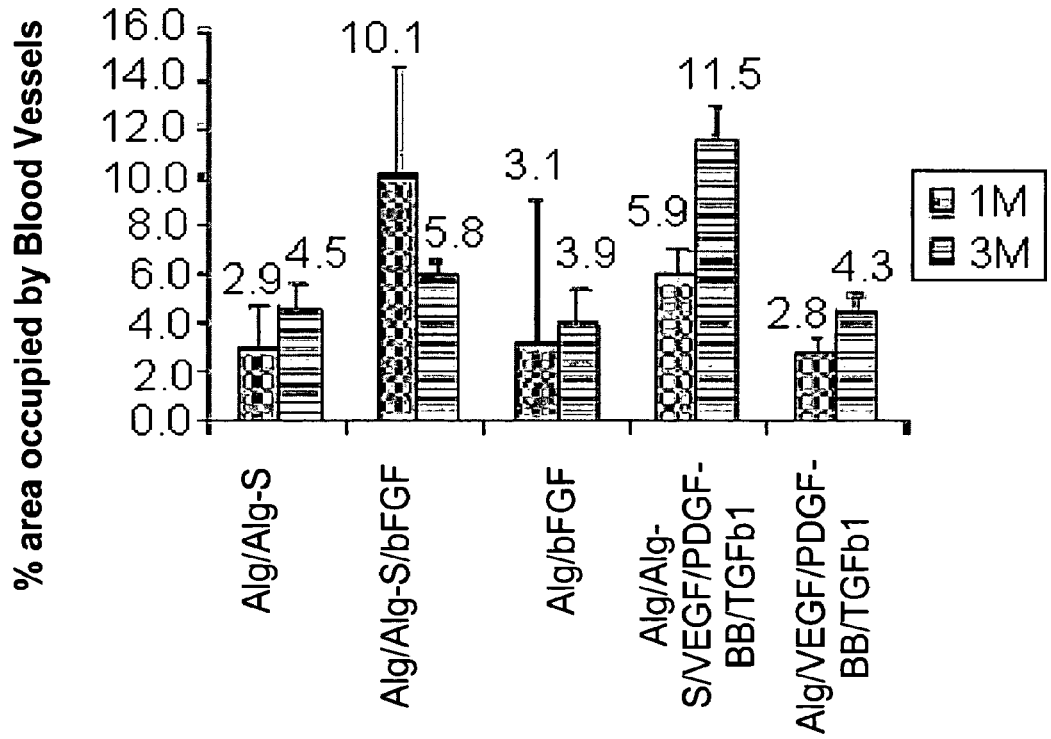
FIG. 27 shows the percentage of the area occupied by blood vessels in the implanted scaffolds, 1 and 3 months post-implantation. P<0.05
Figure 28:
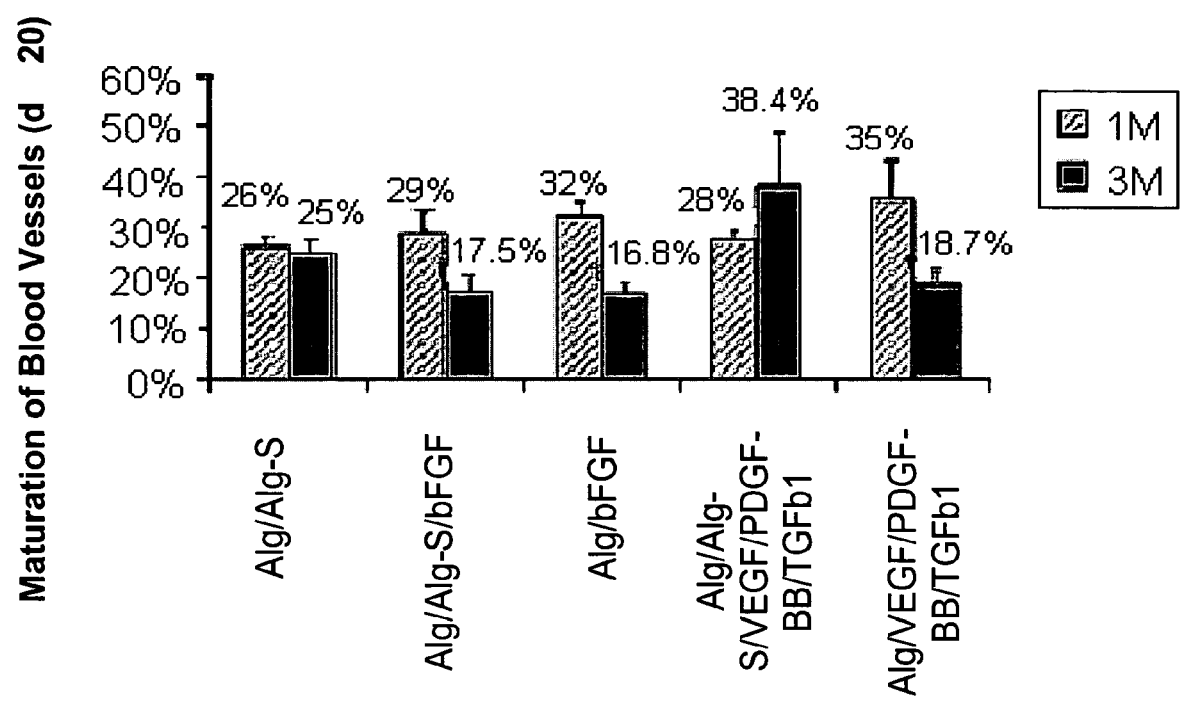
FIG. 28 shows maturation of blood vessels in the implanted scaffolds; 1 and 3 months post-implantation. P<0.05.
Figure 29:
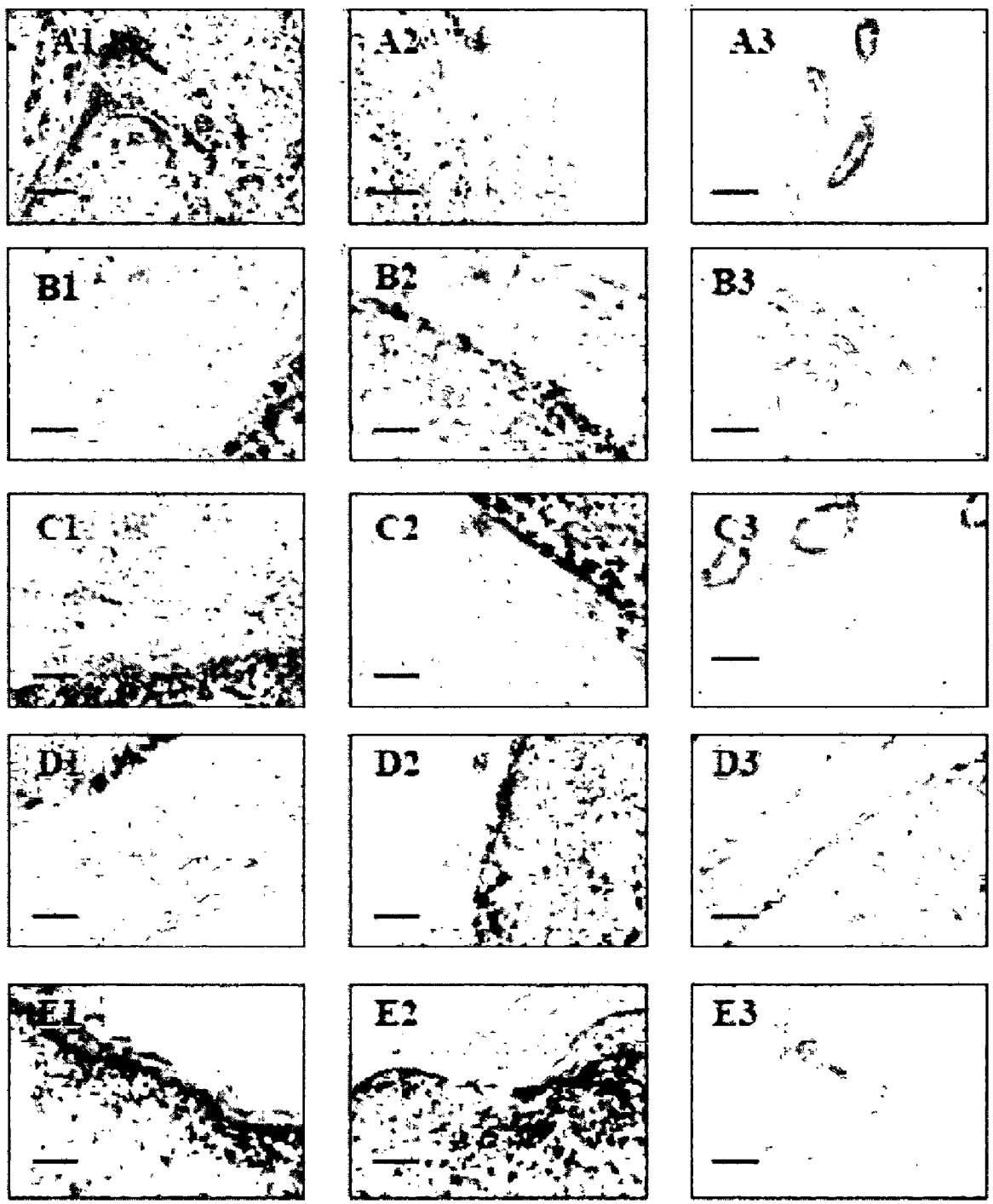
FIGS. 29A-29E show immunohistochemistry analysis of the capsule surrounding the implanted scaffolds 1 month post implantation. α Lectin staining for endothelial cells (29A-29E 1 & 2), αSMA staining for smooth muscle actin (29A3-29E3). (29A) alginate/alginate sulfate/VEGF/PDGF-BB/TGFβ1, (29B) alginate/VEGF/PDGF-BB/TGFβ1 (29C) alginate/alginate sulfate/bFGF (29D) alginate/bFGF (29E) alginate/alginate sulfate. (bar indicates 100 µm).
Figure 30:
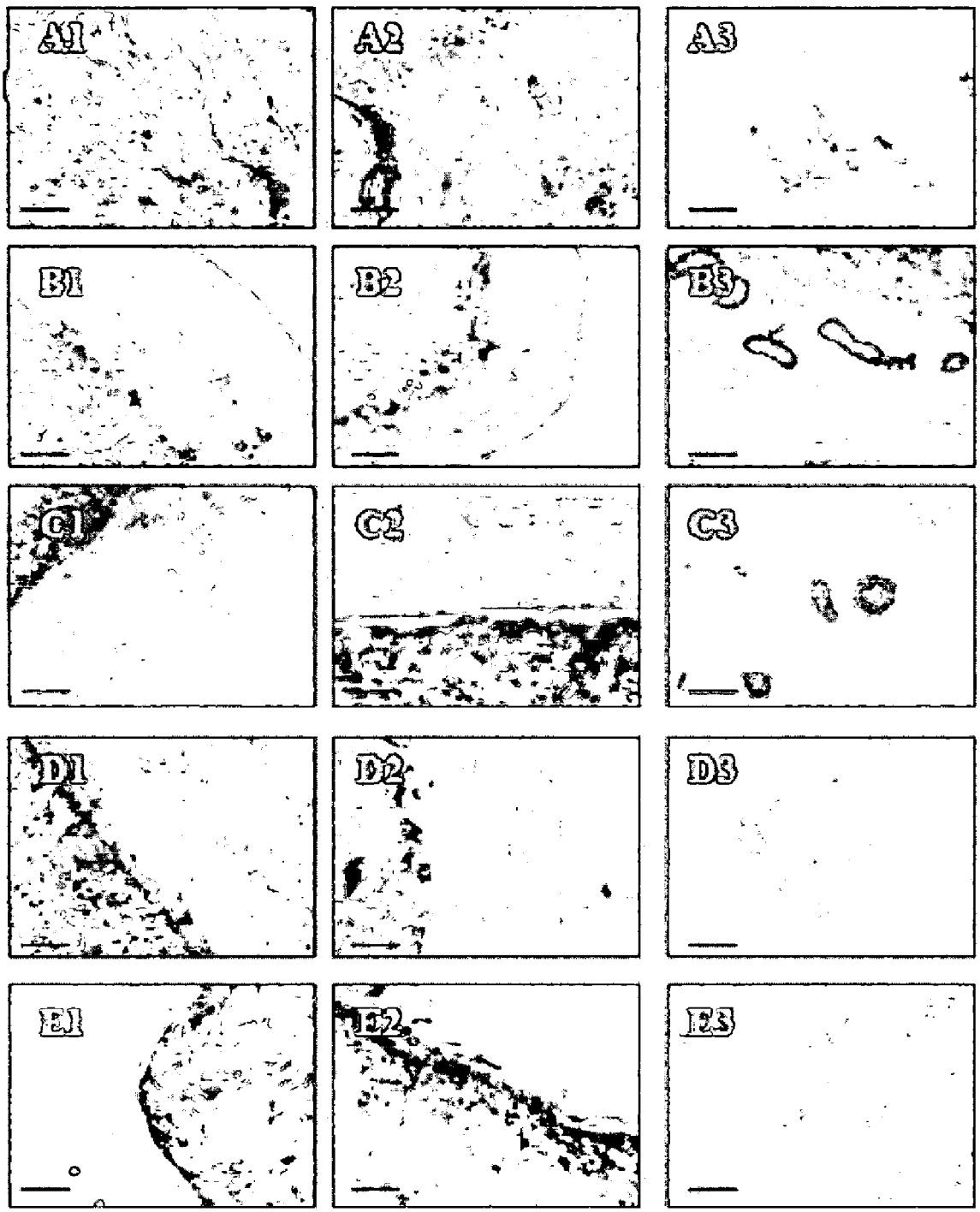
FIGS. 30A-30E show immunohistochemistry of the capsule surrounding the implanted scaffolds 3 months-post implantation. α Lectin staining (30A-30E 1&2), αSMA staining 30A3-30E3. (30A) alginate/alginate sulfate/VEGF/PDGF-BB/TGFβ1, (30B) alginate/VEGF/PDGF-BB/TGFβ1, (30C) alginate/alginate sulfate/bFGF, (30D) alginate/bFGF, and (30E) alginate/alginate sulfate. (bar indicates 100 µm).

At 1 and 3 months post-implantation, the rats were sacrificed and the implanted scaffolds and surrounding tissues were removed together, fixed in formalin, paraffin embedded, sectioned and stained with Hematoxylin and Eosin (H&E) or immunostained for lectin (L-3759, Sigma, Germany). Blood vessel density (number per $mm^2$) (FIG. 26) and the percentage area occupied by them (FIG. 27), were determined from different fields in each slide, randomly selected from the Lectin-immunostained cross sections slides, using Scion image NIH software. Collectively, theses results show that sustained delivery of growth factors from alginate/alginate sulfate scaffolds enhanced angiogenesis at the implant site. One month post-implantation, 115.52±32.52 blood vessels/$mm^2$ was counted in the capsules surrounding the implants of bFGF-bound alginate/alginate sulfate scaffolds. The density of the blood vessels is twice the number found in Experiment #1 (in vivo), although it should be reminded that the amount bFGF used in Experiment #2 is 100-fold less (0.1 vs 10 µg/scaffold). Blood vessel density was less, 75.40±12.44 blood vessels/$mm^2$ in the group implanted with VEGF/PDGF-BB/TGFβ1 bound alginate/alginate sulfate scaffolds. Vessel density was less in the groups wherein the GF were adsorbed to the matrix (and not bound). As shown also in FIG. 26, vessel density was maintained for at least 3 months. According to the percentage area occupied by the blood vessels in cross section (FIG. 27), it is seen that the group receiving the multiple angiogenic factors bound to alginate sulfate, had significant larger blood vessels and most of the vessels were mature (d>20 mm) (FIG. 28). FIGS. 29-30 show immunostaining for lectin and SMA. The positive response indicates the presence mature blood vessels encased by smooth muscle cells.

Example 6

Sulfation of Hyaluronan (Hyaluronic Acid) and Bioconjugation with Bioactive Peptides Hyaluronan (HA), the only non-sulfatedglycosaminoglycan (GAG) and a major component of ECM (extracellular matrix) has been sulfated in order to convert it into a reactive polymer capable of specifically interacting and releasing positively-charged peptides (polypeptides, proteins) and those termed heparin-binding peptides to form a bioconjugate.

For this purpose, we used relatively low molecular HA fragments that have reduced viscosity in solution, thus enabling a better manipulation with the polymer modification as well as better homogeneity in the results. The fragments obtained were characterized by Gel Permeation Chromatography (GPC). Next, we proceeded to sulfation of HA low MW fragments and characterization of degree of sulfation by FTIR (as described above for alginate sulfation). The interaction of HA sulfate and heparin-binding peptides was characterized by SPR technology using the BIAcore 3000 instrument as described above for heparan sulfate. For characterization of the bioconjugates of HA-sulfate and bioactive proteins by SPR, biotinylated HA and biotinylated HA-sulfate immobilized onto streptavidin sensor chip were used.

(i) Obtaining Low Molecular HA Fragments by Heating

Three glass vessels (100 ml erlenmeyer) containing hyaluronan (1% w/v, 10 ml, Cat #53747) were heated at 121° C. for 30', 60 and 90'. Molecular weight (MW) analysis and polydispersity (PDC) was preformed by GPC.

Molecular weight and polydispersity (PDC):

| Treatment | Mw (Dalton) | Mn (Dalton) | PDC (Mw/Mn) |
|---|---|---|---|
| No treatment | $8.612 \times 10^5$ | $8.366 \times 10^5$ | $1.029 \pm 0.005$ |
| 30', 121° C. | $3.403 \times 10^5$ | $3.203 \times 10^5$ | $1.063 \pm 0.003$ |
| 60', 121° C. | $2.019 \times 10^5$ | $1.860 \times 10^5$ | $1.086 \pm 0.003$ |
| 90' 121° C. | $1.202 \times 10^5$ | $1.099 \times 10^5$ | $1.094 \pm 0.003$ |

Further experiments, we carried out with the 120 kDa HA fragments.

(ii) Sulfation of HA Low MW Fragments and Characterization by FTIR

HA sulfation was conducted by the sulfuric acid/carbodiimide method, essentially as described in U.S. Pat. No. 6,388, 060B1 (as described in Example 1).

Figure 31:
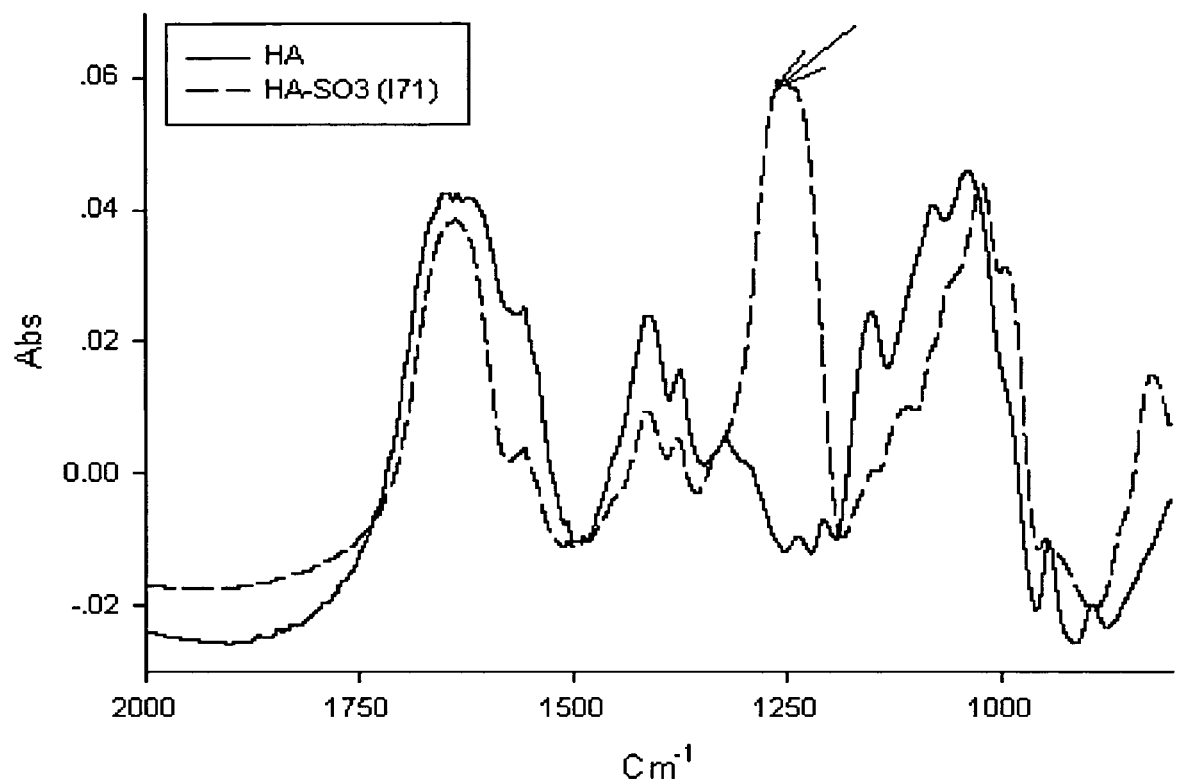
FIG. 31 shows hyaluronan (HA) sulfation and product analysis. FTIR spectra of hyaluronan sulfate (I-71) and raw material hyaluronic acid. The arrow points towards a new major peak at ~1250 cm−1 proving controlled sulfation of HA.

HA-sulfate was characterized by FTIR versus the raw material, low MW HA. The IR spectrum of sulfated HA (FIG. 31) shows a new major peak at ~1250 $cm^{-1}$, which is assigned to S=O symmetric stretching, whiles the one at ~800 $cm^{-1}$ for S—O—C stretching.

For the SPR characterization of the bioconjugates, sulfated and unsulfated HA were biotinylated as described for alginate (as described in Example 2).

Figure 32A:
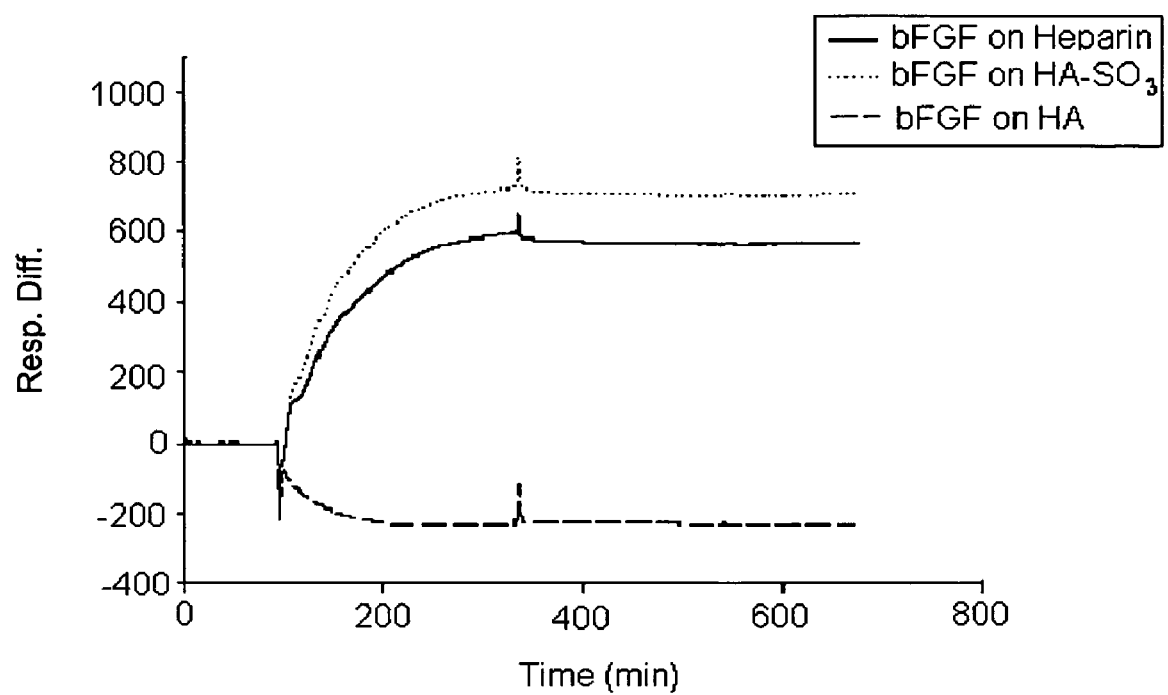
FIGS. 32A-32B show SPR sensorgrams of bFGF binding to hyaluronan-sulfate, over a range of peptide concentrations. (32A) bFGF (700 nM) binding to heparin, hyaluronan (HA)-sulfate and HA immobilized on sensor chip SA. Binding was specific for heparin and hyaluronan sulfate while no interactions with immobilized biotinylated HA were seen. (32B) bFGF was injected over immobilized hyaluronan sulfate. SPR sensorgram presents the affinity profile as a function of bFGF concentrations.
Figure 32B:
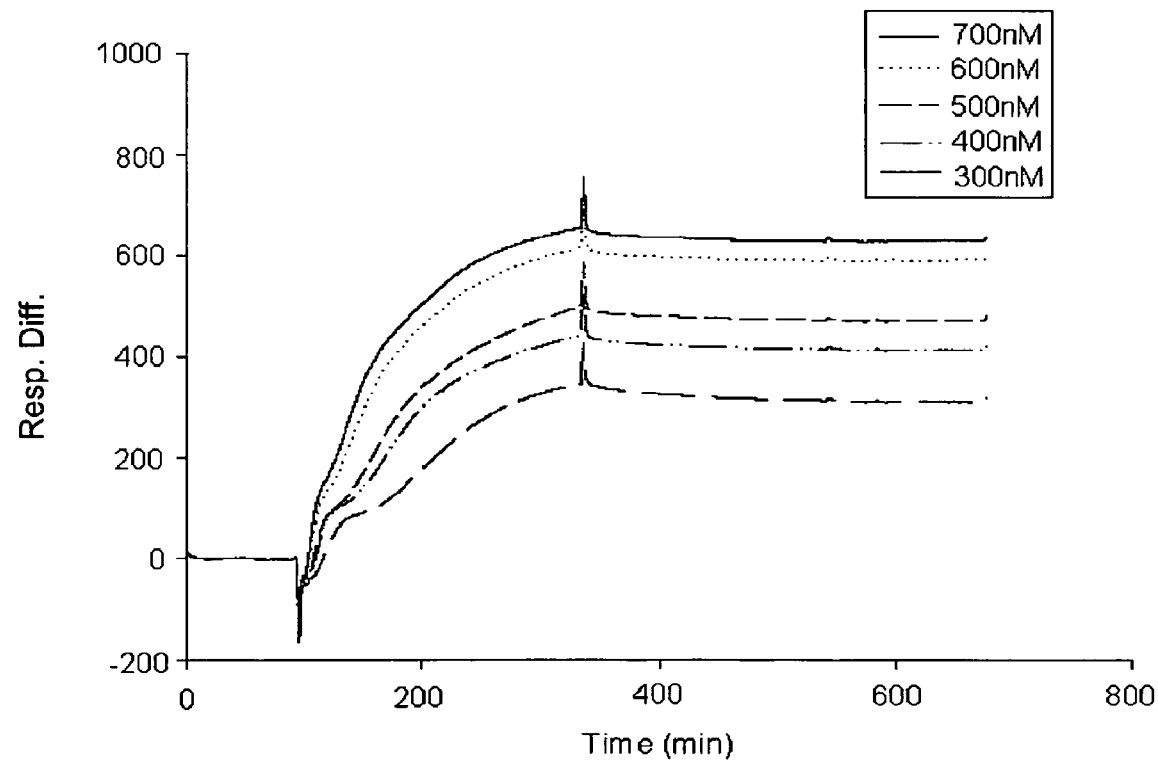
Figure 33A:
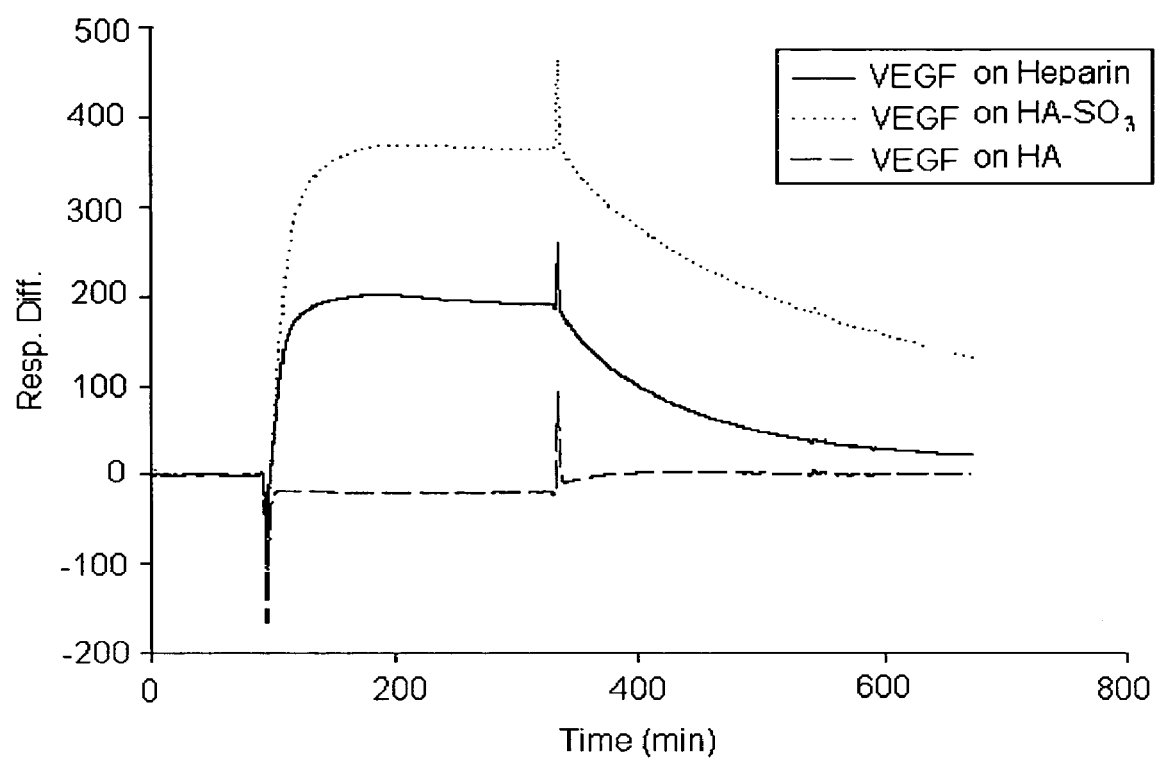
FIGS. 33A-33B show SPR sensorgrams of VEGF binding to hyaluronan-sulfate, over a range of peptide concentrations. (33A) VEGF (100 nM) binding to heparin, hyaluronan (HA)-sulfate and HA immobilized on sensor chip SA. Binding was specific for heparin and hyaluronan sulfate while no interactions with immobilized biotinylated HA were seen. (33B) VEGF was injected over immobilized hyaluronan sulfate. SPR sensorgram presents the affinity profile as a function of VEGF concentrations.
Figure 33B:
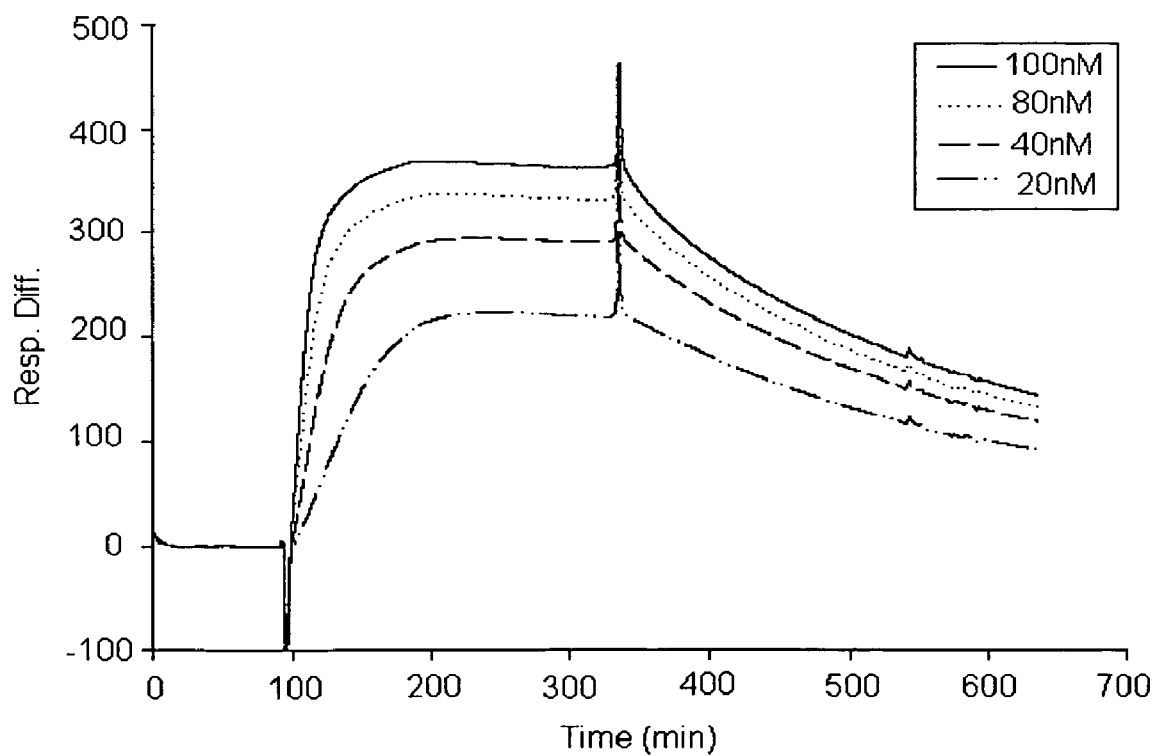

Table 6 summarizes the results obtained in SPR sensorgrams (FIGS. 32 and 33) of peptide binding to sulfated HA, over a range of peptide concentration shows specific binding of sulfated HA to bFGF and sulfated HA to VEGF, while no interactions were found with the nonmodified HA. The SPR sensorgrams (FIG. 32B-33B) of peptide binding to HA-sulfate, over a range of peptide concentrations showed that the interactions fit the Langmuir 1:1 binding model, with equilibrium binding constants detailed in Table 6. We found that the binding of VEGF and bFGF to sulfated HA was stronger than their binding to heparin.

TABLE 6

Bioconjugate Formation. Characterization by SPR

| Peptide | Ligand | $K_A$ (M$^{-1}$) | $K_D$ (M) | $X^2$ | KD (M) (Literature) |
|---|---|---|---|---|---|
| 1 bFGF | Heparin | $1.34 * 10^7$ | $7.46 * 10^{-8}$ | 87.4 | $7.13 * 10^{-8}$ (Xiao-Feng, Ya-xiang et al., 2003) |
| | Ha sulfate | $1.36 * 10^8$ | $7.33 * 10^{-9}$ | 76.5 | |
| 2 VEGF | Heparin | $9.68 * 10^7$ | $1.03 * 10^{-8}$ | 15.8 | |
| | Ha sulfate | $2.11 * 10^8$ | $4.47 * 10^{-9}$ | 23.4 | |

REFERENCES

Akashi, M., and Sakamoto N., et at. (1996). Synthesis and Anticoagulant Activity of Sulfated Glucoside-Bearing Polymer. Bioconjugate Chemistry 7(4): 393-395.

Amara, A., Lorthioir O., et al. (1999). Stromal Cell-derived Factor-1a Associates with Heparan Sulfates through the First b-Strand of the Chemokine. The Journal of Biological Chemistry 274(34): 23916-23925.

Capila I., and Linhardt R. J. (2002). Heparin—Protein Interactions. Angewandte Chem Int. Ed., 41, 390-412.

Geresh, S., Mamontov A., et al. (2002). Sulfation of extracellular polysaccharide of red microalgae: preparation, characterization and properties. Journal of Biochemical and Biophysical Methods 50: 179-187.

Goretzki, L., Burg M. A., et al. (1999). High-affinity Binding of Basic Fibroblast Growth Factor and Platelet-derived Growth Factor-AA to the Core Protein of the NG2 Proteoglycan. The Journal of Biological Chemistry 274(24): 16831-16837.

Kamei, K., Wu X., et al. (2001). The Analysis of Heparin-Protein Interactions Using Evanescent Wave Biosensor with Regioselectivity Desulfated Heparins as the ligand. Analytical Biochemistry 295: 203-213.

Lang, P., Masci G., et al. (1992). Tamarind seed polysaccharide: preparation, characterization and solution properties of carboxy sulphated and alkylaminated derivaties. Carbohydrate Polymers 17: 185-198.

Polyak, B., Geresh, S., and Marks, R. S., (2004). Synthesis and characterization of a biotin-alginate conjugate and its application in a biosensor construction. Biomacromolecules. March-April; 5(2):389-96.

Rahmoune, H., Rudland, P. S., et al. (1998). Hepatocyte Growth Factor/Scatter Factor Has Distinct Classes of Binding Site in Heparan Sulfate from Mammary Cells. Biochemistry 37(17): 6003-6008.

Shapiro, L., and Cohen, S., (1997) Novel alginate sponges for cell culture and transplantation. Biomaterials, 18: 583-590.

Silverstein, R. M., and Webster, F. X., (1997). Spectrometric Identification of Organic Compounds, John Wiley & Sons, Inc. US.

Song, H., Beattie J., et al. (2000). Overlap of IGF- and heparin-binding sites in rat IGF-binding protein-5. Journal of Molecular Endocrinology 24: 43-51.

Wijelath, E. S., Murray J., et al. (2002). Novel Vascular Endothelial Growth Factor Binding Domains of Fibronectin Enhance Vascular Endothelial Growth Factor Biological Activity. Circulation Research 91: 25-31.

Xiao-feng, W., Ya-xiang, X., et al. (2003). Surface Plasmon Resonance Analysis To Evaluate The Importance of Sulfate Groups in Heparin for the Binding with Human aFGF and bFGF. Journal of Zhejiang University Science 1(4): 86-94.

Zhang, F., Fath, M., et al. (2002). A Highly Stable Covalent Conjugated Heparin Biochip for Heparin-Protein Interaction Studies. Analytical Biochemistry 304: 271-273.

The invention claimed is

1. A bioconjugate comprising a sulfated polysaccharide selected from the group consisting of alginate sulfate and hyaluronan sulfate and at least one bioactive polypeptide selected from the group consisting of a positively-charged polypeptide, a heparin-binding polypeptide or both, wherein the bioactive polypeptide non-covalently associates with a sulfate group of the sulfated polysaccharide, thereby allowing sustained release of the bioactive polypeptide from the bioconjugate.

2. The bioconjugate according to claim 1, wherein said at last one bioactive polypeptide is a heparin-binding polypeptide.

3. The bioconjugate according to claim 2, wherein said at least one heparin-binding polypeptide is selected from the group consisting of antithrombin III (AT III), thrombopoietin (TPO), serine protease inhibitor (SLP1), C1 esterase inhibitor (C1 INH), Vaccinia virus complement control protein (VCP), a fibroblast growth factor (FGF), a FGF receptor, vascular endothelial growth factor (VEGF), hepatocyte growth factor (HGF), transforming growth factor β1 (TGF-β1), insulin-like growth factor (IGF), a platelet-derived growth factor (PDGF), epidermal growth factor (EGF), CXC chemokine ligand 4 (CXCL4), stromal cell-derived factor-1 (SDF-1), interleukin-6 (IL-6), interleukin-8 (IL-8), Regulated on Activation, Normal T Expressed and Secreted (RANTES), monocyte chemoattractant protein-1 (MCP-1), macrophage inflammatory peptide-1 (MIP-1), lymphotactin, fractalkine, an annexin, apolipoprotein E (ApoE), immunodeficiency virus type-1 (HIV-1) coat protein gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA, 1-selectin, P-selectin, heparin-binding growth-associated molecule (HB-GAM), thrombospondin type I repeat (TSR), and amyloid P (AP).

4. The bioconjugate according to claim 3, wherein said at least one heparin-binding polypeptide is selected from the group consisting of PDGF-BB, PDGF-AA, bFGF, aFGF, VEGF, TGFβ1, IL-6, TPO, SDF-1, HGF, EGF, and IGF.

5. The bioconjugate according to claim 4, wherein said at least one heparin-binding polypeptide is at least one polypeptide exhibiting angiogenic activity.

6. The bioconjugate according to claim 5, wherein said at least one polypeptide exhibiting angiogenic activity is selected from the group consisting of TGF-BB, VEGF, bFGF, aFGF , PDGF-BB, IGF, and a combination thereof.

7. The bio-conjugate according to claim 6, wherein said at least one polypeptide is bFGF.

8. The bioconjugate according to claim 6, wherein said polypeptide is a combination of VEGF, PDGF-BB, and TGF-β1.

9. The bioconjugate according to claim 1, wherein said at least one bioactive polypeptide is a positively-charged polypeptide selected from the group consisting of insulin, glatiramer acetate, antithrombin III, interferon-γ, IGF, somatostatin, erythropoietin, luteinizing hormone-releasing hormone, IL-2, and IL-6.

10. The bioconjugate according to claim 1, wherein the bioconjugate is selected from the group consisting of aFGF-alginate sulfate, bFGF-alginate sulfate, PDGF-BB-alginate sulfate, PDGF-AA-alginate sulfate, VEGF-alginate sulfate, TGFβ1-alginate sulfate, IL-6-alginate sulfate, TPO-alginate sulfate, SDF-1-alginate sulfate, HGF-alginate sulfate, EGF-alginate sulfate, IGF-alginate sulfate, bFGF-hyaluronan sulfate and VEGF-hyaluronan sulfate.

11. A pharmaceutical composition comprising a bioconjugate according to claim 1, and a pharmaceutically acceptable carrier.

12. The pharmaceutical composition according to claim 11 as a delivery system for sustained release of at least one bioactive polypeptide, composed of a bioconjugate comprising said at least one bioactive polypeptide selected from the group consisting of a positively-charged polypeptide, a heparin-binding polypeptide or both, and a sulfated polysaccharide selected from the group consisting of alginate sulfate and hyaluronan sulfate, wherein the bioactive polypeptide non-covalently associates with a sulfate group of the sulfated polysaccharide, thereby allowing sustained release of the bioactive polypeptide from the bioconjugate.

13. The pharmaceutical composition according to claim 12, wherein said at least one bioactive polypeptide is a heparin-binding polypeptide.

14. The pharmaceutical composition according to claim 13, wherein said at least one heparin-binding polypeptide is selected from the group consisting of antithrombin III (AT III), thrombopoietin (TPO), serine protease inhibitor (SLP1), C1 esterase inhibitor (C1 INH), Vaccinia virus complement control protein (VCP) , a fibroblast growth factor (FGF), a FGF receptor, vascular endothelial growth factor (VEGF), hepatocyte growth factor (HGF), transforming growth factor β1 (TGF-β1), insulin-like growth factor (IGF), a platelet-derived growth factor (PDGF), epidermal growth factor (EGF), CXC chemokine ligand 4 (CXCL4), stromal cell-derived factor-1 (SDF-1), interleukin-6 (IL-6), interleukin-8 (IL-8), Regulated on Activation, Normal T Expressed and Secreted (RANTES), monocyte chemoattractant protein-1 (MCP-1), macrophage inflammatory peptide-1 (MIP-1), lymphotactin, fractalkine, an annexin, apolipoprotein E (ApoE), immunodeficiency virus type-1 (HIV-1) coat protein gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA, 1-selectin, P-selectin, heparin-binding growth-associated molecule (HB-GAM), thrombospondin type I repeat (TSR), and amyloid P (AP).

15. The pharmaceutical composition according to claim 14, wherein said at least one heparin-binding polypeptide is selected from the group consisting of PDGF-BB, PDGF-AA, bFGF, aFGF, VEGF, TGFβ1, IL-6, TPO, SDF-1, HGF, EGF, and IGF.

16. The pharmaceutical composition according to claim 12, wherein said at least one bioactive polypeptide is a positively-charged polypeptide selected from the group consisting of insulin, glatiramer acetate, antithrombin III, interferon-γ, IGF, somatostatin, erythropoietin, luteinizing hormone-releasing hormone, IL-2, and IL-6.

17. The pharmaceutical composition according to claim 12, wherein said bioconjugate is provided in a supporting matrix.

18. The pharmaceutical composition according to claim 17, wherein the supporting matrix is a polymer selected from the group consisting of a polysaccharide, a protein, an extracellular matrix component, a synthetic polymer, and a mixture thereof.

19. The pharmaceutical composition according to claim 18, wherein said supporting matrix polymer is alginate hydrogel or hyaluronan hydrogel.

20. A pharmaceutical composition comprising a sulfated polysaccharide selected from the group consisting of sulfated alginate, sulfated hyaluronan, and both, and a pharmaceutically acceptable carrier, for treatment or inhibition of a disease or disorder caused by, or associated with, the activity of at least one bioactive polypeptide capable of non-covalently associates with a sulfate group of said sulfated polysaccharide.

21. The pharmaceutical composition according to claim 20, wherein the disease or disorder is caused by or associated with the activity of a bioactive polypeptide selected from the group consisting of platelet-derived growth factor BB (PDGF-BB), basic fibroblast growth factor (bFGF), vascular endothelial growth factor (VEGF), transforming growth factor β (TGFβ), acidic fibroblast growth factor (aFGF), interleukin-6 (IL-6), thrombopoietin (TPO), stromal cell derived factor-1 (SDF-1), hepatocyte growth factor (HGF), epidermal growth factor (EGF), insulin like growth factor (IGF), platelet-derived growth factor AA (PDGF-AA), and a combination thereof.

22. A method of sustained release administration of at least one bioactive polypeptide capable of non-covalently associating with a sulfate group of a sulfated polysaccharide to a patient in need of treatment with said polypeptide, wherein the method comprises administering to said patient an effective amount of a bioconjugate of claim 1.

23. A bioconjugate comprising a sulfated polysaccharide selected from the group consisting of alginate sulfate and hyaluronan sulfate and at least one bioactive heparin-binding polypeptide, wherein the bioactive heparin-binding polypeptide non-covalently associates with a sulfate group of the sulfated polysaccharide, thereby allowing sustained release of the bioactive heparin-binding polypeptide from the bioconjugate.

* * * * *